(12) United States Patent
Kato et al.

(10) Patent No.: US 6,284,112 B1
(45) Date of Patent: Sep. 4, 2001

(54) GAS SENSOR

(75) Inventors: Nobuhide Kato, Ama-gun; Yasuhiko Hamada, Nagoya, both of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/251,376

(22) Filed: Feb. 17, 1999

(30) Foreign Application Priority Data

Feb. 19, 1998 (JP) .................................................. 10-037735

(51) Int. Cl.[7] .................................................. G01N 27/407
(52) U.S. Cl. .......................... 204/425; 204/426; 204/427; 204/429; 205/781; 205/786.5
(58) Field of Search ..................... 204/421–429

(56) References Cited

U.S. PATENT DOCUMENTS

| | | | |
|---|---|---|---|
| 4,324,632 | * 4/1982 | Tantram et al. | 204/415 |
| 5,314,604 | * 5/1994 | Friese et al. | 204/426 |
| 5,672,811 | 9/1997 | Kato et al. . | |
| 5,676,811 | * 10/1997 | Makino et al. | 204/425 |
| 5,763,763 | 6/1998 | Kato et al. . | |

FOREIGN PATENT DOCUMENTS

| | | |
|---|---|---|
| 0 678 740 | 4/1995 | (EP) . |
| 0 769 693 | 4/1997 | (EP) . |
| 8-271476 | 10/1996 | (JP) . |
| 9-113484 | 5/1997 | (JP) . |

* cited by examiner

*Primary Examiner*—T. Tung
(74) *Attorney, Agent, or Firm*—Burr & Brown

(57) ABSTRACT

Disclosed is a gas sensor for measuring a NOx concentration comprising a main pumping cell and a detecting electrode, the main pumping cell including an electrode (an inner pumping electrode and an outer pumping electrode) having no decomposing/reducing ability for NOx or a low decomposing/reducing ability for NOx, to be used so that an oxygen concentration in a first chamber is controlled to have a predetermined value at which NO is not substantially decomposable, and the detecting electrode having a certain decomposing/reducing ability for NOx or a high decomposing/reducing ability for NOx, to be used so that NOx is decomposed to measure the NOx concentration by measuring an amount of oxygen produced during this process, wherein a buffering space is provided between a gas-introducing port and the first chamber. Accordingly, it is possible to avoid any influence of exhaust gas pressure pulsation generated in a measurement gas and improve the measurement accuracy on the detecting electrode.

11 Claims, 24 Drawing Sheets

GAS SENSOR

BACKGROUND OF THE INVENTION

1. Field of the Invention

The present invention relates to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

Those hitherto known as the method for measuring NOx in a measurement gas such as combustion gas include a technique in which the NOx-reducing ability of Rh is utilized in a sensor comprising a Pt electrode and an Rh electrode formed on an oxygen ion-conductive solid electrolyte such as zirconia so that an electromotive force generated between the electrodes is measured.

However, the sensor as described above suffers the following problems. That is, the electromotive force is greatly changed depending on the change in concentration of oxygen contained in the combustion gas as the measurement gas. Moreover, the change in electromotive force is small with respect to the change in concentration of NOx. For this reason, the conventional sensor tends to suffer influence of noise.

Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform accurate measurement for a combustion gas produced under such a combustion condition.

In order to solve the problems as described above, for example, Japanese Laid-Open Patent Publication No. 8-271476 discloses a NOx sensor comprising pumping electrodes having different NOx-decomposing abilities arranged in a first internal space which communicates with a measurement gas-existing space and in a second internal space which communicates with the first internal space, and a method for measuring the NOx concentration in which the $O_2$ concentration is adjusted by using a first pumping cell arranged in the first internal space, and NO is decomposed by using a decomposing pumping cell arranged in the second internal space so that the NOx concentration is measured on the basis of a pumping current flowing through the decomposing pump.

Further, Japanese Laid-Open Patent Publication No. 9-113484 discloses a sensor element comprising an auxiliary pumping electrode arranged in a second internal space so that the oxygen concentration in the second internal space is controlled to be constant even when the oxygen concentration is suddenly changed.

In general, the gas sensor is affected by any pulsation or fluctuation of the exhaust gas pressure generated in a measurement gas when the gas sensor is practically used in a vehicle or an automobile. As a result, the oxygen existing in the external space suddenly enters the fist space of the gas sensor.

In order to solve this problem, for example, there have been hitherto adopted an arrangement in which the diffusion rate-determining section provided between the gas-introducing port and the first space is composed of a porous member, and an arrangement in which the diffusion rate-determining section is formed to have a slit-shaped configuration or the diffusion rate-determining section is formed by inserting a porous member into a slit.

However, it has been revealed that the influence of the exhaust gas pressure pulsation cannot be effectively avoided even when the arrangement as described above is adopted, because of the following reason. That is, when the pressure in the external space is positive as compared with the pressure in the first space due to the exhaust gas pressure pulsation, the oxygen in the external space suddenly enters the first space as if it protrudes toward the first space.

The pressure in the external space is negative as compared with the pressure in the first space at the point of time of completion of the protruding supply of oxygen to the first space. However, the oxygen, which has been once supplied to the first space, is not discharged through the diffusion rate-determining section via a route opposite to the supply route. Therefore, in such a case, the oxygen is merely pumped out to the external space by means of the pumping action effected by a main pump. The main pump performs the pumping process so that the oxygen concentration in the first space is a predetermined concentration. However, a certain degree of time is required to allow the oxygen concentration to arrive at the predetermined concentration. During this period of time, a phenomenon occurs, in which the oxygen is suddenly supplied to the first space again due to the exhaust gas pressure pulsation. Consequently, it is impossible to efficiently perform the operation for controlling the oxygen concentration in the first space to be the predetermined concentration by using the main pump.

As a result, it is inevitable that the correlation is deteriorated between the oxygen concentration in the measurement gas and the oxygen pumping amount effected by the main pump in the first space. It is feared that the disturbance of the oxygen concentration in the first space may cause deterioration concerning the control of oxygen concentration in the second space which communicates with the first space, and concerning the measurement accuracy on the detecting electrode which serves as a NOx-detecting section.

SUMMARY OF THE INVENTION

The present invention has been made taking the foregoing problems into consideration, an object of which is to provide a gas sensor which makes it possible to avoid any influence of exhaust gas pressure pulsation generated in a measurement gas and improve the measurement accuracy on a detecting electrode.

According to the present invention, there is provided a gas sensor comprising a main pumping means for pumping-processing oxygen contained in a measurement gas introduced from an external space via a gas-introducing port into a processing space formed and comparted by solid electrolytes contacting with the external space so that a partial pressure of oxygen in the processing space is controlled to have a predetermined value at which a predetermined gas component as a measurement objective is not decomposable; and an electric signal-generating conversion means for making conversion into an electric signal corresponding to an amount of oxygen contained in the measurement gas after being pumping-processed by the main pumping means; wherein a measurement gas component contained in the measurement gas is measured on the basis of the electric signal supplied from the electric signal-generating conversion means; the gas sensor further comprising a buffering space provided between the gas-introducing port and the processing space.

According to the present invention, at first, the oxygen, which is contained in the measurement gas introduced from the external space, is pumping-processed by the main pumping means, and the oxygen is adjusted to have a predetermined concentration. The measurement gas, which has been adjusted for the oxygen concentration by the main pumping means, is introduced into the electric signal-generating conversion means in the next step. The electric signal-generating conversion means decomposes the measurement gas component contained in the introduced measurement gas by means of catalytic action and/or electrolysis, to make conversion into the electric signal corresponding to the amount of oxygen produced by the decomposition. The measurement gas component contained in the measurement gas is measured on the basis of the electric signal supplied from the electric signal-generating conversion means.

The predetermined gas component includes, for example, NO, and the measurement gas component includes, for example, NOx.

When the electric signal-generating conversion means comprises a measuring pumping means, the measurement gas, which has been adjusted for the oxygen concentration by the main pumping means, is introduced into the measuring pumping means.

The measuring pumping means decomposes the measurement gas component after being pumping-processed by the main pumping means, by means of catalytic action and/or electrolysis, and it pumping-processes oxygen produced by the decomposition. The predetermined gas component corresponding to an amount of oxygen is measured on the basis of a pumping current generated in the measuring pumping means in accordance with the amount of oxygen pumping-processed by the measuring pumping means.

In another aspect, the electric signal-generating conversion means comprises a concentration-detecting means. In this case, the measurement gas, which has been adjusted for the oxygen concentration by the main pumping means, is introduced into the concentration-detecting means in the next step. An electromotive force of an oxygen concentration cell is generated in the concentration-detecting means, which corresponds to a difference between an amount of oxygen contained in a reference gas and an amount of oxygen produced by decomposition of the predetermined gas component contained in the measurement gas. The measurement gas component corresponding to the amount of oxygen is measured on the basis of the electromotive force.

In the meantime, the oxygen suddenly enters the sensor element via the gas-introducing port on account of the pulsation of the exhaust gas pressure in the external space. However, the oxygen from the external space does not directly enter the processing space, but it enters the buffering space which is disposed at the upstream stage thereof. In other words, the sudden change in oxygen concentration due to the exhaust gas pressure pulsation is counteracted by the buffering space. The influence of the exhaust gas pressure pulsation on the processing space is in a degree of almost negligible.

As a result, the oxygen-pumping amount effected by the main pumping means in the processing space is well correlated with the oxygen concentration in the measurement gas, and it is possible to improve the measurement accuracy obtained by using the measuring pumping means. Simultaneously, the processing space can be commonly used, for example, as a sensor for determining the air-fuel ratio.

It is preferable for the gas sensor according to the present invention that a first diffusion rate-determining section for giving a predetermined diffusion resistance to the measurement gas is provided on an introducing route for the measurement gas into the buffering space, and a second diffusion rate-determining section for giving a predetermined diffusion resistance to the measurement gas is provided on an introducing route for the measurement gas from the buffering space into the processing space.

In this case, the buffering space has its volume which is determined on the basis of at least each of the diffusion resistances of the first diffusion rate-determining section and the second diffusion rate-determining section.

It is also preferable that the buffering space has its front opening which constitutes the gas-introducing port, and the first diffusion rate-determining section is formed so that the gas-introducing port is covered therewith.

It is also preferable that the first and second diffusion rate-determining sections are formed as narrow communication passages respectively. In this case, it is preferable that the respective communication passages are formed so that a position of the communication passage for constructing the first diffusion rate-determining section is not coincident with a position of the communication passage for constructing the second diffusion rate-determining section as viewed on projection planes opposed to a direction of introduction of the gas.

Each of the first and second diffusion rate-determining sections may be made of a porous member.

It is desirable for the gas sensor described above that an area of a projection plane of the buffering space, which is opposed to a direction of introduction of the gas, is not less than an area of a projection plane of the processing space, which is opposed to the direction of introduction of the gas. Accordingly, the volume of the buffering space is increased. Therefore, the function to counteract the exhaust gas pressure pulsation is effectively exhibited, and thus it is possible to eliminate almost all influences of the exhaust gas pressure pulsation on the processing space.

In another aspect, the gas sensor may be constructed such that a clogging-preventive section and a buffering space are provided in series between the gas-introducing port and the processing space, the gas-introducing port is formed at a front opening of the clogging-preventive section, and a diffusion rate-determining section for giving a predetermined diffusion resistance to the measurement gas is provided between the clogging-preventive section and the buffering space.

In this aspect, the gas sensor is prevented from clogging of particles (for example, soot and oil combustion waste) produced in the measurement gas in the external space, which would be otherwise caused at the inlet of the buffering space or in the vicinity thereof. Thus, it is possible to measure the predetermined gas component more accurately.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Explanation will be made below with reference to FIGS. 1 to 29 for several illustrative embodiments in which the gas sensor according to the present invention is applied to gas sensors for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

Figure 1:
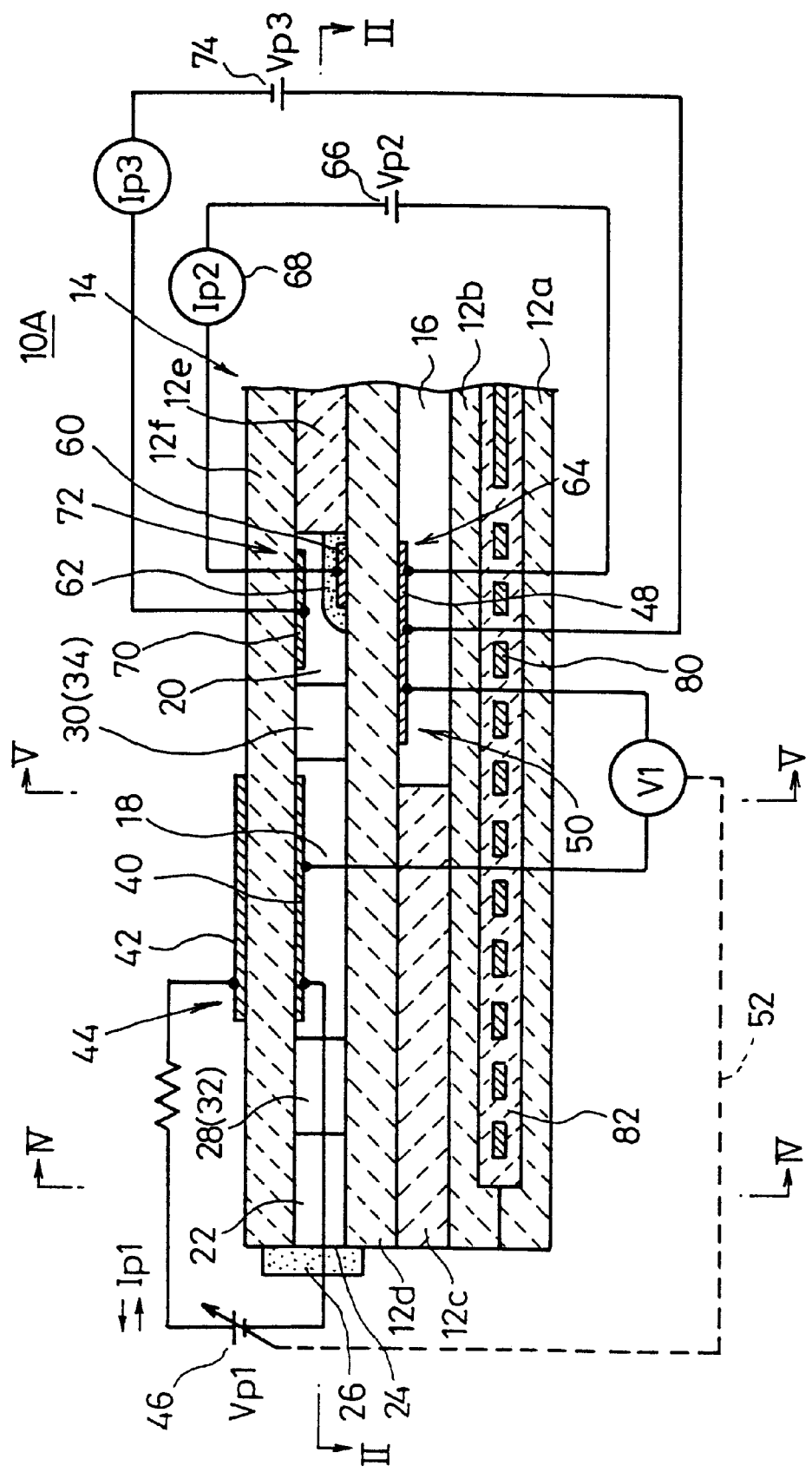
FIG. 1 shows a sectional view illustrating an arrangement of a gas sensor according to a first embodiment.
Figure 2:
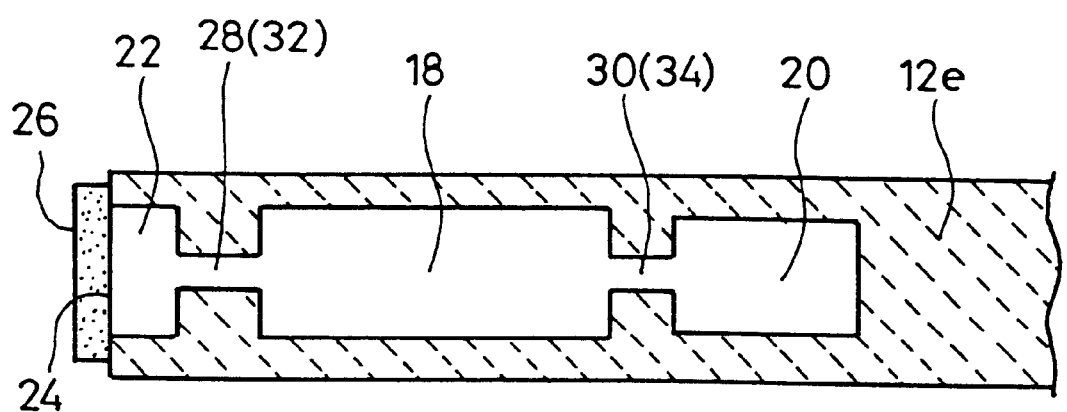
FIG. 2 show sa sectional view taken along a line II—II shown in FIG. 1.
Figure 3:
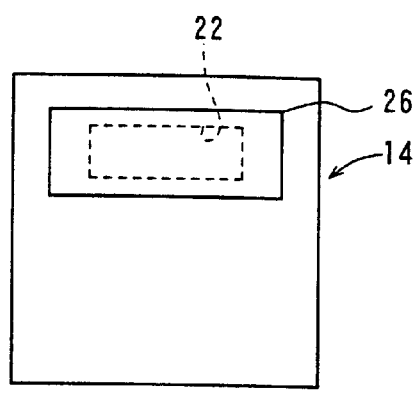
FIG. 3 shows a front view illustrating the gas sensor according to the first embodiment.
Figure 4:
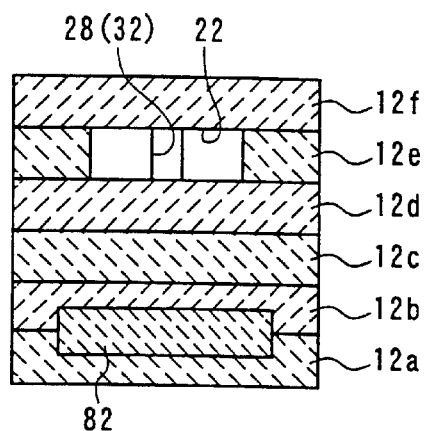
FIG. 4 shows a sectional view taken along a line IV—IV shown in FIG. 1.
Figure 5:
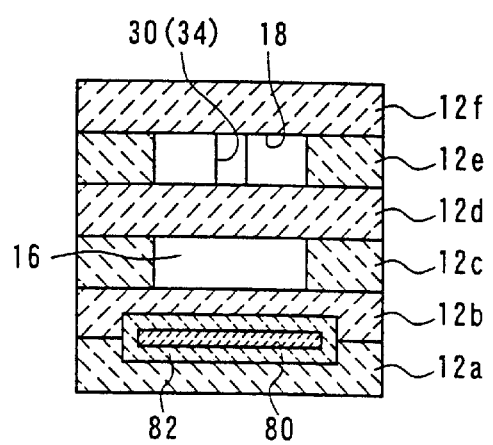
FIG. 5 shows a sectional view taken along a line V—V shown in FIG. 1.

As shown in FIG. 1, a gas sensor 10A according to the first embodiment includes a sensor element 14 comprising, for example, six stacked solid electrolyte layers 12a to 12f composed of ceramics based on the use of oxygen ion-conductive solid electrolytes such as $ZrO_2$.

In the sensor element 14, first and second layers from the bottom are designated as first and second substrate layers 12a, 12b respectively. Third and fifth layers from the bottom are designated as first and second spacer layers 12c, 12e respectively. Fourth and sixth layers from the bottom are designated as first and second solid electrolyte layers 12d, 12f respectively.

A space (reference gas-introducing space) 16, into which a reference gas such as atmospheric air to be used as a reference for measuring oxides is introduced, is formed between the second substrate layer 12b and the first solid electrolyte layer 12d, the space 16 being comparted by a lower surface of the first solid electrolyte layer 12d, an upper surface of the second substrate layer 12b, and side surfaces of the first spacer layer 12c.

A first chamber 18 for adjusting the partial pressure of oxygen in a measurement gas is formed and comparted between a lower surface of the second solid electrolyte layer 12f and an upper surface of the first solid electrolyte layer 12d. A second chamber 20 for finely adjusting the partial pressure of oxygen in the measurement gas and measuring oxides, for example, nitrogen oxides (NOx) in the measurement gas is formed and comparted between the lower surface of the second solid electrolyte layer 12f and the upper surface of the first-solid electrolyte layer 12d.

The gas sensor 10A according to the first embodiment comprises a buffering space 22 which is formed at the front end of the second spacer layer 12e. A front end opening of the buffering space 22 constitutes a gas-introducing port 24. A first diffusion rate-determining section 26 is formed so that the gas-introducing port 24 is covered therewith.

The buffering space 22 communicates with the first chamber 18 via a second diffusion rate-determining section 28. The first chamber 18 communicates with the second chamber 20 via a third diffusion rate-determining section 30. That is, the buffering space 22 is formed at the front end of the second spacer layer 12e, and it is comparted by the lower surface of the second solid electrolyte layer 12f, the upper surface of the first solid electrolyte layer 12d, the first diffusion rate-determining section 26, and the second diffusion rate-determining section 28.

The first diffusion rate-determining section 26 gives a predetermined diffusion resistance to the measurement gas introduced into the buffering space 22. In this embodiment, as shown in FIG. 1, the first diffusion rate-determining section 26 is made of a porous material (for example, an ARON ceramic material) through which the measurement gas can be introduced. On the other hand, the second and third diffusion rate-determining sections 28, 30 give predetermined diffusion resistances to the measurement gas introduced into the first chamber 18 and the second chamber 20 respectively. In this embodiment, as shown in FIGS. 2, 3, 4, and 5, each of them is formed as a slit 32 or 34 which has a vertical length longer than a horizontal length and which has a predetermined cross-sectional area so that the measurement gas may be introduced thereinto. Both of the slits 32, 34 are formed at substantially central portions in the widthwise direction of the second spacer layer 12e.

A porous member composed of, for example, $ZrO_2$ may be charged and arranged in the slit 34 of the third diffusion rate-determining section 30 so that the diffusion resistance of the third diffusion rate-determining section 30 may be larger than the diffusion resistance of the second diffusion rate-determining section 28. The diffusion resistance of the third diffusion rate-determining section 30 is preferably larger than that of the second diffusion rate-determining section 28. However, no trouble occurs even when the former is smaller than the latter.

The atmosphere in the first chamber 18 is introduced into the second chamber 20 under the predetermined diffusion resistance via the third diffusion rate-determining section 30.

An inner pumping electrode 40 having a substantially rectangular planar configuration and composed of a porous cermet electrode (for example, a cermet electrode of Pt•$ZrO_2$ containing 1% Au) is formed on the entire lower surface portion for forming the first chamber 18, of the lower surface of the second solid electrolyte layer 12f. An outer pumping electrode 42 is formed on a portion corresponding to the inner pumping electrode 40, of the upper surface of the second solid electrolyte layer 12f. An electrochemical pumping cell, i.e., a main pumping cell 44 is constructed by the inner pumping electrode 40, the outer pumping electrode 42, and the second solid electrolyte layer 12f interposed between the both electrodes 40, 42.

A desired control voltage (pumping voltage) Vp1 is applied between the inner pumping electrode 40 and the outer pumping electrode 42 of the main pumping cell 44 by the aid of an external variable power source 46 to allow a pumping current Ip1 to flow in a positive or negative direction between the outer pumping electrode 42 and the inner pumping electrode 40. Thus, the oxygen in the atmosphere in the first chamber 18 can be pumped out to the external space, or the oxygen in the external space can be pumped into the first chamber 18.

A reference electrode 48 is formed on a lower surface portion exposed to the reference gas-introducing space 16, of the lower surface of the first solid electrolyte layer 12d. An electrochemical sensor cell, i.e., a controlling oxygen partial pressure-detecting cell 50 is constructed by the inner pumping electrode 40, the reference electrode 48, the second solid electrolyte layer 12f, the second spacer layer 12e, and the first solid electrolyte layer 12d.

The controlling oxygen partial pressure-detecting cell 50 is operated as follows. That is, an electromotive force is generated between the inner pumping electrode 40 and the reference electrode 48 on the basis of a difference in oxygen concentration between the atmosphere in the first chamber 18 and the reference gas (atmospheric air) in the reference gas-introducing space 16. The partial pressure of oxygen in the atmosphere in the first chamber 18 can be detected by using the electromotive force.

The detected value of the partial pressure of oxygen is used to feedback-control the variable power source 46. Specifically, the pumping operation effected by the main pumping cell 44 is controlled by the aid of a feedback control system 52 for the main pump so that the partial pressure of oxygen in the atmosphere in the first chamber 18 has a predetermined value which is sufficiently low to control the partial pressure of oxygen in the second chamber in the next step.

The feedback control system 52 comprises a circuit constructed to feedback-control the pumping current Vp1 between the outer pumping electrode 42 and the inner pumping electrode 40 so that a difference (detection voltage V1) between an electric potential of the inner pumping electrode 40 and an electric potential of the reference electrode 48 is at a predetermined voltage level. In this embodiment, the inner pumping electrode 40 is grounded.

Therefore, the main pumping cell 44 pumps out or pumps in oxygen in an amount corresponding to the level of the pumping voltage Vp1, of the measurement gas introduced into the first chamber 18. The oxygen concentration in the first chamber 18 is subjected to feedback control to give a predetermined level by repeating the series of operations described above. In this state, the pumping current Ip1, which flows between the outer pumping electrode 42 and the inner pumping electrode 40, indicates the difference between the oxygen concentration in the measurement gas and the controlled oxygen concentration in the first chamber 18. The pumping current Ip1 can be used to measure the oxygen concentration in the measurement gas.

Each of the inner pumping electrode 40 and the outer pumping electrode 42 is composed of a porous cermet electrode which is made of a metal such as Pt and a ceramic such as $ZrO_2$. It is necessary to use a material which has a weak reducing ability or no reducing ability with respect to the NO component in the measurement gas, for the inner pumping electrode 40 disposed in the first chamber 18 to make contact with the measurement gas. It is preferable that the inner pumping electrode 40 is composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

In the gas sensor 10A according to the first embodiment, a detecting electrode 60 having a substantially rectangular planar configuration and composed of a porous cermet electrode is formed at a portion separated from the third diffusion rate-determining section 30, on an upper surface portion for forming the second chamber 20, of the upper surface of the first solid electrolyte layer 12d. An alumina film for constructing a fourth diffusion rate-determining section 62 is formed so that the detecting electrode 60 is covered therewith. An electrochemical pumping cell, i.e., a measuring pumping cell 64 is constructed by the detecting electrode 60, the reference electrode 48, and the first solid electrolyte layer 12d.

The detecting electrode 60 is composed of a porous cermet comprising zirconia as a ceramic and a metal capable of reducing NOx as the measurement gas component. Accordingly, the detecting electrode 60 functions as a NOx-reducing catalyst for reducing NOx existing in the atmosphere in the second chamber 20. Further, the oxygen in the atmosphere in the second chamber 20 can be pumped out to the reference gas-introducing space 16 by applying a constant voltage Vp2 between the detecting electrode 60 and the reference electrode 48 by the aid of a DC power source 66. The pumping current Ip2, which is allowed to flow in accordance with the pumping operation performed by the measuring pumping cell 64, is detected by an ammeter 68.

The constant voltage (DC) power source 66 can apply a voltage of a magnitude to give a limiting current to the pumping for oxygen produced during decomposition in the measuring pumping cell 64 under the inflow of NOx restricted by the fourth diffusion rate-determining section 62.

On the other hand, an auxiliary pumping electrode 70 having a substantially rectangular planar configuration and composed of a porous cermet electrode (for example, a cermet electrode of Pt•$ZrO_2$ containing 1% Au) is formed on the entire lower surface portion for forming the second chamber 20, of the lower surface of the second solid electrolyte layer 12f. An auxiliary electrochemical pumping cell, i.e., an auxiliary pumping cell 72 is constructed by the auxiliary pumping electrode 70, the second solid electrolyte layer 12f, the second spacer layer 12e, the first solid electrolyte layer 12d, and the reference electrode 48.

The auxiliary pumping electrode 70 is based on the use of a material having a weak reducing ability or no reducing ability with respect to the NO component contained in the measurement gas, in the same manner as in the inner pumping electrode 40 of the main pumping cell 44. In this embodiment, it is preferable that the auxiliary pumping electrode 70 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35% by volume of the entire metal components.

A desired constant voltage Vp3 is applied between the reference electrode 48 and the auxiliary pumping electrode 70 of the auxiliary pumping cell 72 by the aid of an external DC power source 74. Thus, the oxygen in the atmosphere in the second chamber 20 can be pumped out to the reference gas-introducing space 16.

Accordingly, the partial pressure of oxygen in the atmosphere in the second chamber 20 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 44 for the first chamber 18, the change in amount of oxygen introduced into the second chamber 20 is greatly reduced as compared with the change in the measurement gas. Accordingly, the partial pressure of oxygen in the second chamber 20 is accurately controlled to be constant.

Therefore, in the gas sensor 10A according to the first embodiment constructed as described above, the measurement gas, for which the partial pressure of oxygen has been controlled in the second chamber 20, is introduced into the detecting electrode 60.

As shown in FIG. 1, the gas sensor 10A according to the first embodiment further comprises a heater 80 for generating heat in accordance with electric power supply from the outside. The heater 80 is embedded in a form of being vertically interposed between the first and second substrate layers 12a, 12b. The heater 80 is provided in order to increase the conductivity of oxygen ion. An insulative layer 82 composed of alumina or the like is formed to cover upper and lower surfaces of the heater 80 so that the heater 80 is electrically insulated from the first and second substrate layers 12a, 12b.

The heater 80 is arranged over the entire portion ranging from the first chamber 18 to the second chamber 20. Accordingly, each of the first chamber 18 and the second chamber 20 is heated to a predetermined temperature. Simultaneously, each of the main pumping cell 44, the controlling oxygen partial pressure-detecting cell 50, and the measuring pumping cell 64 is also heated to a predetermined temperature and maintained at that temperature.

Next, the operation of the gas sensor 10A according to the first embodiment will be explained. At first, the forward end of the gas sensor 10A is disposed in the external space. Accordingly, the measurement gas is introduced into the first chamber 18 under the predetermined diffusion resistance via the first diffusion rate-determining section 26, the buffering space 22, and the second diffusion rate-determining section 28 (slit 32). The measurement gas, which has been introduced into the first chamber 18, Is subjected to the pumping action for oxygen, caused by applying the predetermined pumping voltage Vp1 between the outer pumping electrode 42 and the inner pumping electrode 40 which construct the main pumping cell 44. The partial pressure of oxygen is controlled to have a predetermined value, for example, $10^{-7}$ atm. The control is performed by the aid of the feedback control system 52.

The second diffusion rate-determining section 28 serves to limit the amount of diffusion and inflow of oxygen in the measurement gas into the measuring space (first chamber 18) when the pumping voltage Vp1 is applied to the main pumping cell 44 so that the current flowing through the main pumping cell 44 is suppressed.

In the first chamber 18, a state of partial pressure of oxygen is established, in which NOx in the atmosphere is not reduced by the inner pumping electrode 40 in an environment of being heated by the external measurement gas and being heated by the heater 80. For example, a condition of partial pressure of oxygen is formed, in which the reaction of NO→½N$_2$+½O$_2$ does not occur, because of the following reason. That is, if NOx in the measurement gas (atmosphere) is reduced in the first chamber 18, it is impossible to accurately measure NOx in the second chamber 20 disposed at the downstream stage. In this context, it is necessary to establish a condition in the first chamber 18 in which NOx is not reduced by the component which participates in reduction of NOx (in this case, the metal component of the inner pumping electrode 40). Specifically, as described above, such a condition is achieved by using, for the inner pumping electrode 40, the material having a low ability to reduce NOx, for example, an alloy of Au and Pt.

The gas in the first chamber 18 is introduced into the second chamber 20 under the predetermined diffusion resistance via the third diffusion rate-determining section 30. The gas, which has been introduced into the second chamber 20, is subjected to the pumping action for oxygen, caused by applying the voltage Vp3 between the reference electrode 48 and the auxiliary pumping electrode 70 which constitute the auxiliary pumping cell 72 to make fine adjustment so that the partial pressure of oxygen has a constant and low value of partial pressure of oxygen.

The third diffusion rate-determining section 30 serves to limit the amount of diffusion and inflow of oxygen in the measurement gas into the measuring space (second chamber 20) when the voltage Vp3 is applied to the auxiliary pumping cell 72 so that the pumping current Ip3 flowing through the auxiliary pumping cell 72 is suppressed, in the same manner as performed by the second diffusion rate-determining section 28.

The measurement gas, which has been controlled for the partial pressure of oxygen in the second chamber 20 as described above, is introduced into the detecting electrode 60 under the predetermined diffusion resistance via the fourth diffusion rate-determining section 62.

When it is intended to control the partial pressure of oxygen in the atmosphere in the first chamber 18 to have a low value of the partial pressure of oxygen which does not substantially affect the measurement of NOx, by operating the main pumping cell 44, in other words, when the pumping voltage Vp1 of the variable power source 46 is adjusted by the aid of the feedback control system 52 so that the voltage V1 detected by the controlling oxygen partial pressure-detecting cell 50 is constant, if the oxygen concentration in the measurement gas greatly changes, for example, in a range of 0 to 20%, then the respective partial pressures of oxygen in the atmosphere in the second chamber 20 and in the atmosphere in the vicinity of the detecting electrode 60 slightly change in ordinary cases. This phenomenon is caused probably because of the following reason. That is, when the oxygen concentration in the measurement gas increases, the distribution of the oxygen concentration occurs in the widthwise direction and in the thickness direction in the first chamber 18. The distribution of the oxygen concentration changes depending on the oxygen concentration in the measurement gas.

However, in the case of the gas sensor 10A according to the first embodiment, the auxiliary pumping cell 72 is provided for the second chamber 20 so that the partial pressure of oxygen in its internal atmosphere always has a constant low value of the partial pressure of oxygen. Accordingly, even when the partial pressure of oxygen in the atmosphere introduced from the first chamber 18 into the second chamber 20 changes depending on the oxygen concentration in the measurement gas, the partial pressure of oxygen in the atmosphere in the second chamber 20 can be always made to have a constant low value, owing to the pumping action performed by the auxiliary pumping cell 72. As a result, the partial pressure of oxygen can be controlled to have a low value at which the measurement of NOx is not substantially affected.

NOx in the measurement gas introduced into the detecting electrode 60 is reduced or decomposed around the detecting electrode 60. Thus, for example, a reaction of NO →½N$_2$+ ½O$_2$ is allowed to occur. In this process, a predetermined voltage Vp2, for example, 430 mV (700° C.) is applied between the detecting electrode 60 and the reference electrode 48 which construct the measuring pumping cell 64, in a direction to pump out the oxygen from the second chamber 20 to the reference gas-introducing space 16.

Therefore, the pumping current Ip2 flowing through the measuring pumping cell 64 has a value which is proportional to a sum of the oxygen concentration in the atmosphere introduced Into the second chamber 20, i.e., the oxygen concentration in the second chamber 20 and the oxygen concentration produced by reduction or decomposition of NOx by the aid of the detecting electrode 60.

In this embodiment, the oxygen concentration in the atmosphere in the second chamber 20 is controlled to be constant by means of the auxiliary pumping cell 72. Accordingly, the pumping current Ip2 flowing through the measuring pumping cell 64 is proportional to the NOx concentration. The NOx concentration corresponds to the amount of diffusion of NOx limited by the fourth diffusion rate-determining section 62. Therefore, even when the oxygen concentration in the measurement gas greatly changes, it is possible to accurately measure the NOx concentration, based on the use of the measuring pumping cell 64 by the aid of the ammeter 68.

According to the fact described above, almost all of the pumping current value Ip2 obtained by operating the measuring pumping cell 64 represents the amount brought about by the reduction or decomposition of NOx. Accordingly, the obtained result does not depend on the oxygen concentration in the measurement gas.

In the meantime, the gas sensor 10A according to the first embodiment undergoes the exhaust gas pressure pulsation in the external space. As a result, the oxygen suddenly enters the sensor element 14 via the gas-introducing port 24. However, the oxygen from the external space does not directly enter the first chamber 18, but it enters the buffering space 22 disposed at the upstream thereof. That is, the sudden change in oxygen concentration, which is caused by the exhaust gas pressure pulsation, is counteracted by the buffering space 22. Thus, the influence of the exhaust gas pressure pulsation on the first chamber 18 is in an almost negligible degree.

As a result, the oxygen-pumping amount effected by the main pumping cell 44 for the first chamber 18 is well correlated with the oxygen concentration in the measurement gas, and it is possible to improve the measurement accuracy obtained by using the measuring pumping cell 64. Simultaneously, the first chamber 18 can be commonly used, for example, as a sensor for determining the air-fuel ratio.

Two illustrative experiments (conveniently referred to as "first Illustrative experiment" and "second illustrative experiment") will now be described. The first illustrative experiment relates to Working Example 1 and Comparative Example, in order to plot values of the pumping current Ip1 flowing through the main pumping cell 44 when the concentration of oxygen contained in the measurement gas was changed. Obtained results are shown in FIG. 6A (Comparative Example) and FIG. 6B (Working Example 1).

Figure 7A:
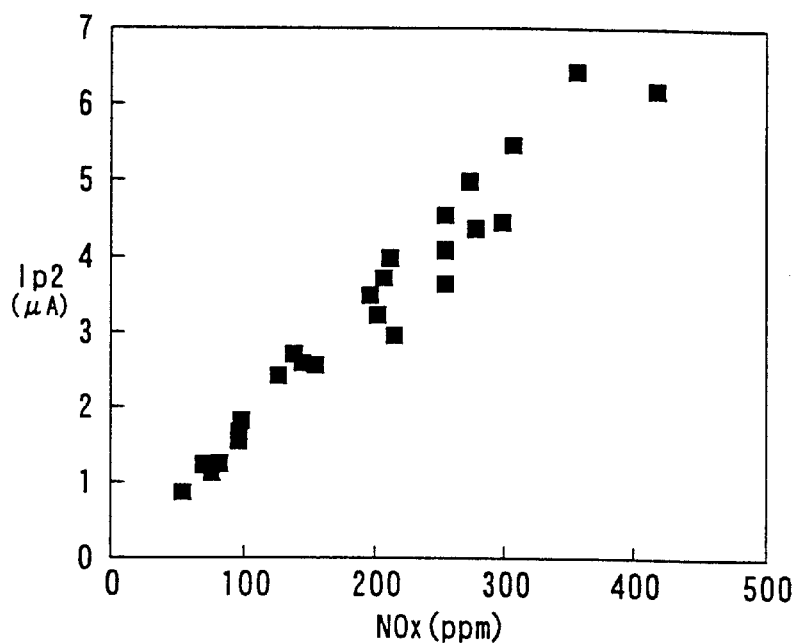
FIG. 7A shows a characteristic illustrating a result of a second illustrative experiment to observe the value of the detection current flowing through a measuring pumping cell, obtained when the concentration of oxygen contained in the measurement gas is changed for the gas sensor concerning Comparative Example.

The second illustrative experiment relates to Working Example 1 and Comparative Example, in order to plot values of the detection current Ip2 flowing through the measuring pumping cell 64 when the concentration of oxygen contained in the measurement gas was changed. Obtained results are shown in FIG. 7A (Comparative Example) and FIG. 7B (Working Example 1).

Comparative Example was arranged such that the first diffusion rate-determining section 26 was removed from the gas sensor 10A according to the first embodiment, and the buffering space 22 was not provided at the upstream of the first chamber 18. Working Example 1 was arranged in the same manner as the gas sensor 10A according to the first embodiment.

Figure 6A:
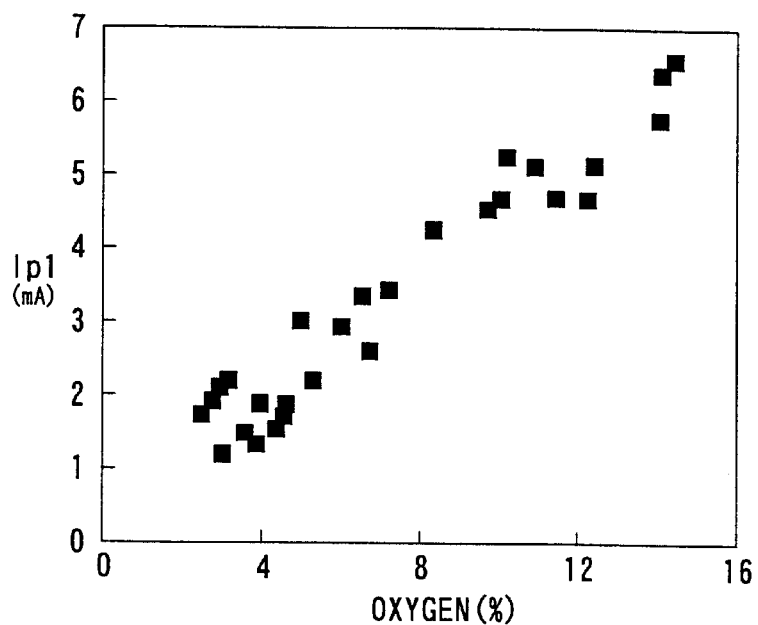
FIG. 6A shows a characteristic illustrating a result of a first illustrative experiment to observe the value of the pumping current flowing through a main pumping cell, obtained when the concentration of oxygen contained in the measurement gas is changed for a gas sensor concerning Comparative Example.

According to the results of these experiments, the following fact is understood for Comparative Example as shown in FIG. 6A. That is, the value of the pumping current Ip1 involves large dispersion even when the oxygen concentration is identical, and the correlation between the oxygen concentration and the pumping current Ip1 tends to disappear. Therefore, as shown in FIG. 7A, the detection current Ip2 also involves dispersion, and the measurement accuracy for NOx is deteriorated. This results from the fact that the first chamber 18 is directly affected by the influence caused by the exhaust gas pressure pulsation in the external space.

Figure 6B:
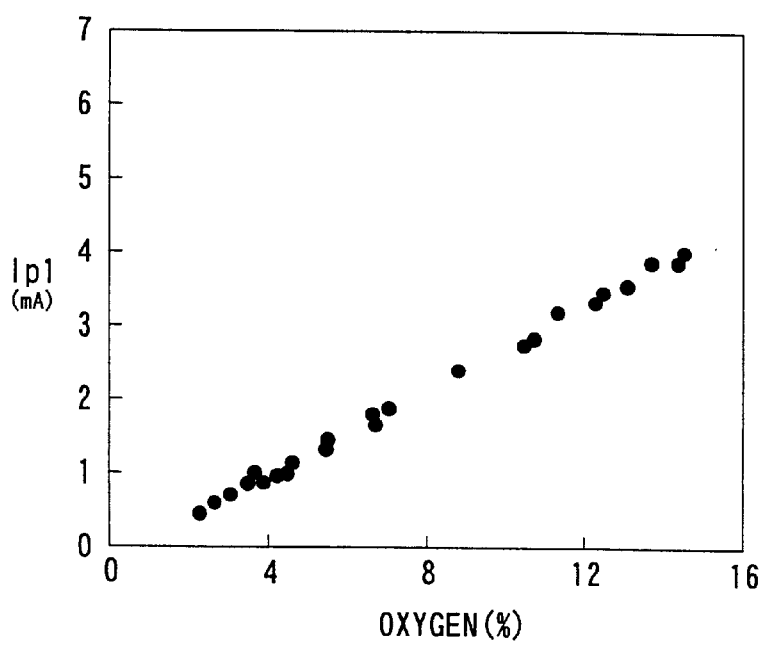
FIG. 6B shows a characteristic illustrating a result of the first illustrative experiment, obtained for a gas sensor concerning Working Example 1.
Figure 7B:
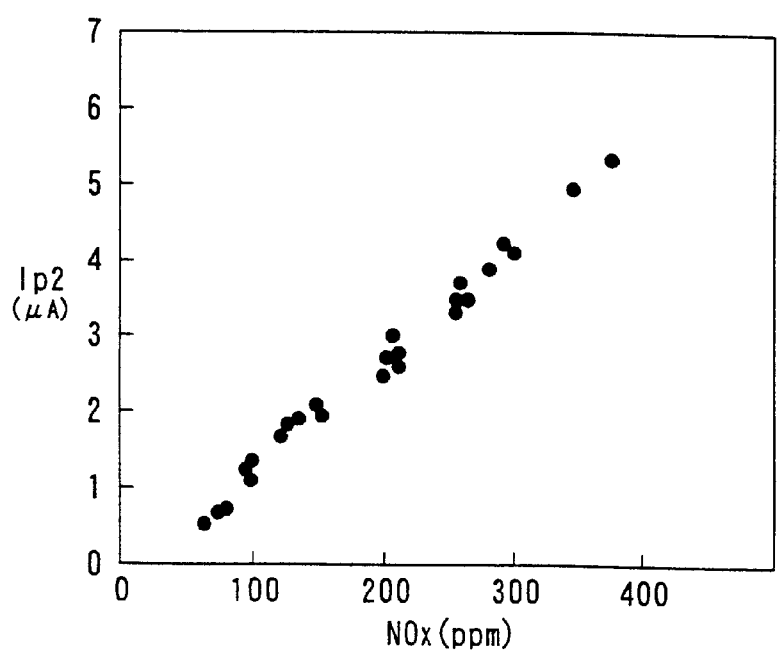
FIG. 7B shows a characteristic illustrating a result of the second illustrative experiment, obtained for the gas sensor concerning Working Example 1.

On the contrary, the following fact is understood for Working Example 1 as shown in FIG. 6B. That is, the value of the pumping current Ip1 is well correlated with the oxygen concentration. As a result, as shown in FIG. 7B, the detection current Ip2 hardly involves dispersion. This results from the fact that the presence of the buffering space 22 counteracts almost all influences which would be otherwise caused by the exhaust gas pressure pulsation in the external space.

Next, a modified embodiment 10Aa of the gas sensor 10A according to the first embodiment will be explained with reference to FIG. 8. Components or parts corresponding to those shown in FIG. 1 are designated by the same reference numerals, duplicate explanation of which will be omitted.

Figure 8:
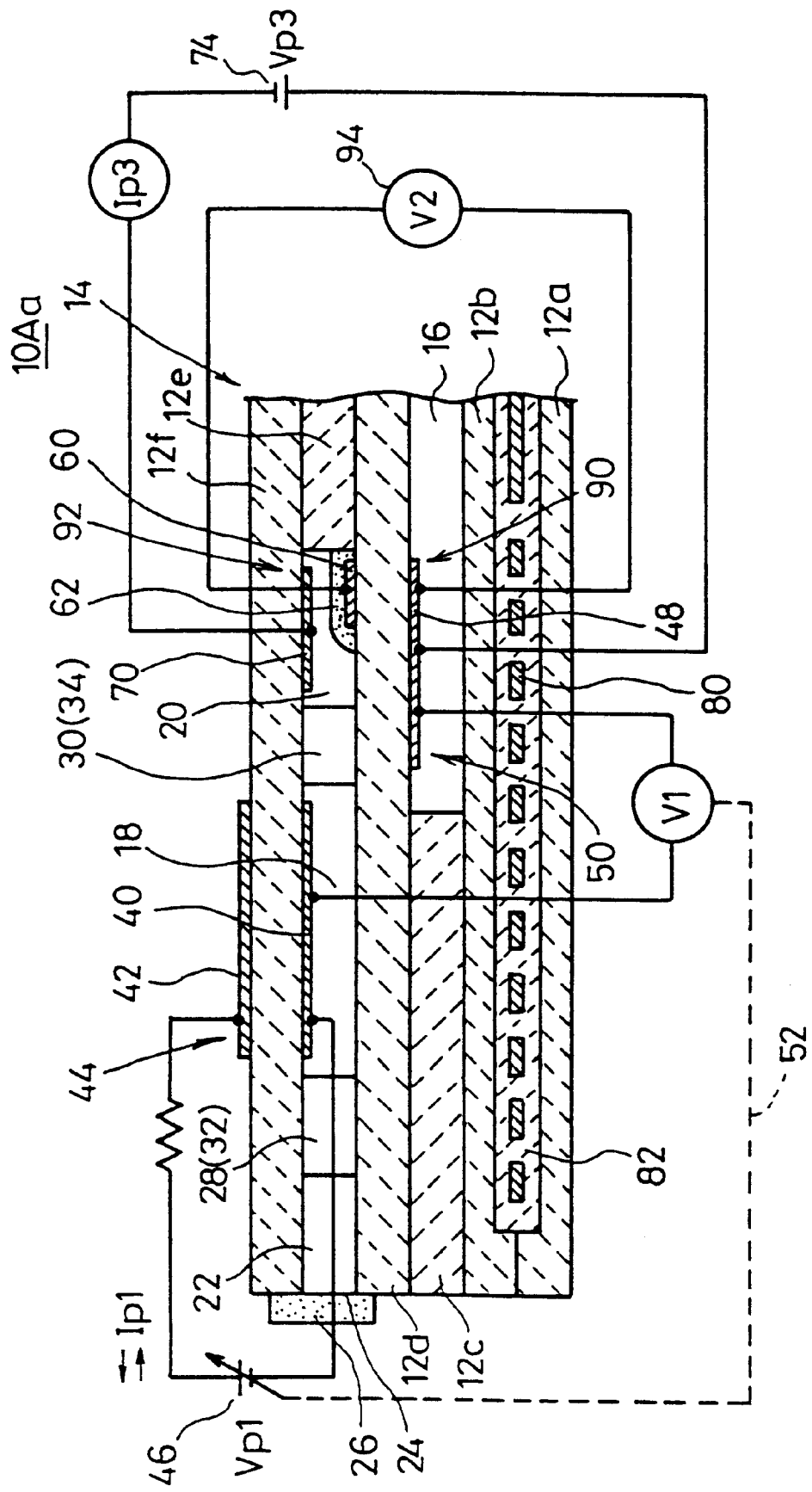
FIG. 8 shows a sectional view illustrating a modified embodiment of the gas sensor according to the first embodiment.

As shown in FIG. 8, a gas sensor 10Aa according to the modified embodiment is constructed in approximately the same manner as the gas sensor 10A according to the first embodiment (see FIG. 1). However, the former is different from the latter in that a measuring oxygen partial pressure-detecting cell 90 is provided in place of the measuring pumping cell 64.

The measuring oxygen partial pressure-detecting cell 90 comprises a detecting electrode 92 formed on an upper surface portion for forming the second chamber 20, of the upper surface of the first solid electrolyte layer 12d, the reference electrode 48 formed on the lower surface of the first solid electrolyte layer 12d, and the first solid electrolyte layer 12d interposed between the both electrodes 92, 48.

In this embodiment, an electromotive force (electromotive force of an oxygen concentration cell) V2 corresponding to the difference in oxygen concentration between the atmosphere around the detecting electrode 92 and the atmosphere around the reference electrode 48 is generated between the reference electrode 48 and the detecting electrode 92 of the measuring oxygen partial pressure-detecting cell 90.

Therefore, the partial pressure of oxygen in the atmosphere around the detecting electrode 92, in other words, the partial pressure of oxygen defined by oxygen produced by reduction or decomposition of the measurement gas component (NOx) is detected as a voltage value V2 by measuring the electromotive force (voltage V2) generated between the detecting electrode 92 and the reference electrode 48 by using a voltmeter 94.

The gas sensor 10Aa according to the modified embodiment also includes the buffering space 22 disposed between the gas-introducing port 24 and the first chamber 18. Therefore, the sudden change in oxygen concentration due to the exhaust gas pressure pulsation is counteracted by the buffering space 22, and the influence of the exhaust gas pressure pulsation on the first chamber 18 is in an almost negligible degree.

As a result, the oxygen-pumping amount effected by the main pumping cell 44 for the first chamber 18 is well correlated with the oxygen concentration in the measurement gas, and it is possible to improve the measurement accuracy obtained by using the measuring oxygen partial pressure-detecting cell 90, in the same manner as in the gas sensor 10A according to the first embodiment. Simultaneously, the first chamber 18 can be commonly used, for example, as a sensor for determining the air-fuel ratio as well.

Next, a gas sensor 10B according to the second embodiment will be explained with reference to FIGS. 9 to 14B. Components or parts corresponding to those shown in FIG. 1 are designated by the same reference numerals, duplicate explanation of which will be omitted.

Figure 9:
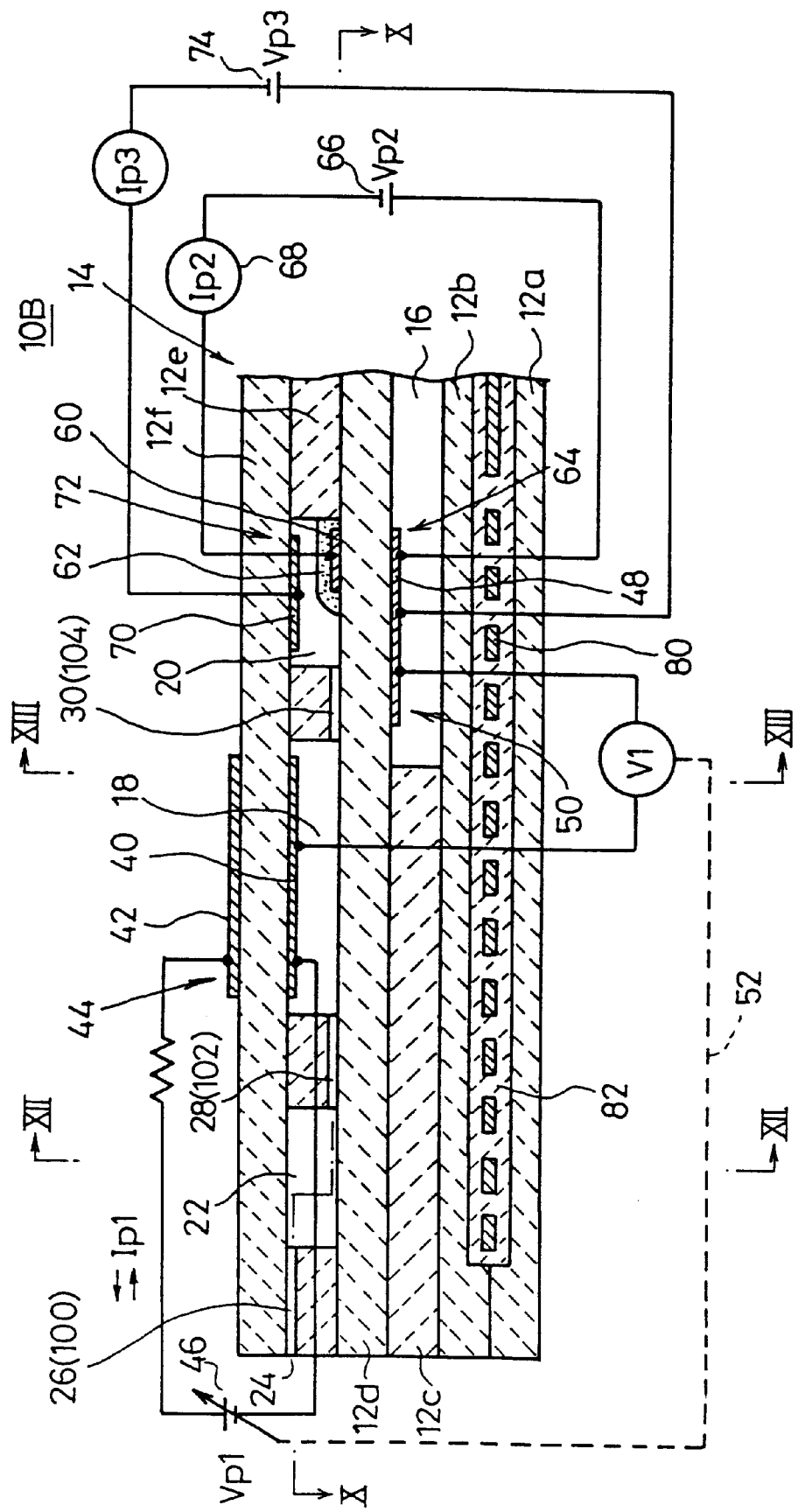
FIG. 9 shows a sectional view illustrating an arrangement of a gas sensor according to a second embodiment.
Figure 10:
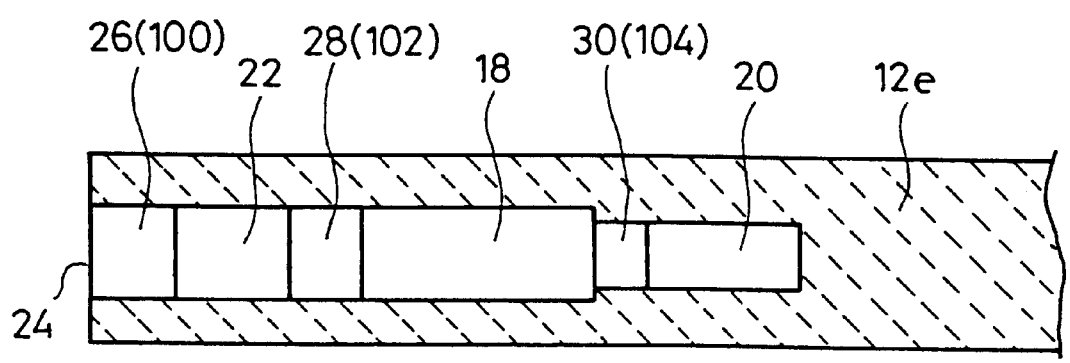
FIG. 10 shows a sectional view taken along a line X—X shown in FIG. 9.

As shown in FIGS. 9 and 10, the gas sensor 10B according to the second embodiment is constructed in approximately the same manner as the gas sensor 10A according to the first embodiment (see FIG. 1). However, the former is different from the latter in the following points.

Figure 11:
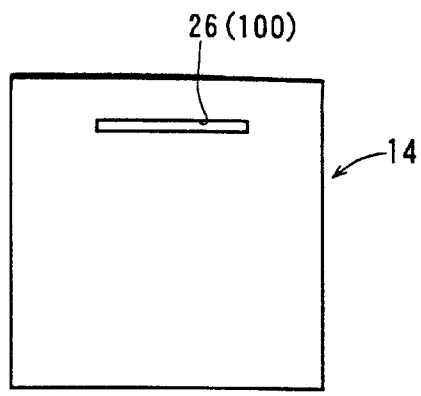
FIG. 11 shows a front view illustrating the gas sensor according to the second embodiment.
Figure 12:
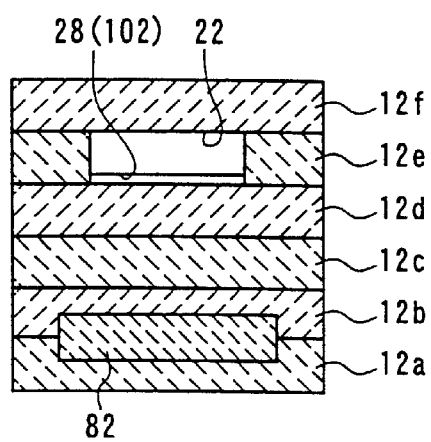
FIG. 12 shows a sectional view taken along a line XII—XII shown in FIG. 9.
Figure 13:
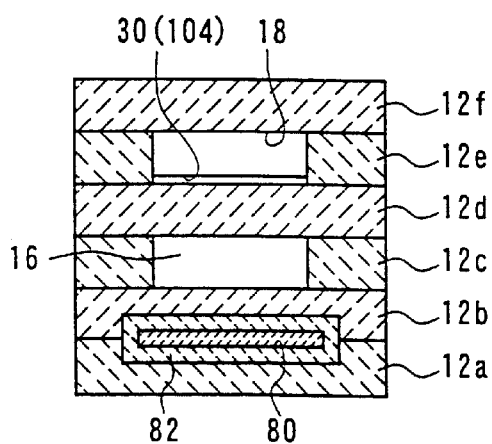
FIG. 13 shows a sectional view taken along a line XIII—XIII shown in FIG. 9.

Firstly, as also shown in FIG. 11, the first diffusion rate-determining section 26 is constructed as a communication hole 100 having a horizontal length longer than a vertical length formed at a portion contacting with the lower surface of the second solid electrolyte layer 12f at the front end of the second spacer layer 12e. Secondly, as also shown In FIG. 12, the second diffusion rate-determining section 28 is constructed as a communication hole 102 having a horizontal length longer than a vertical length formed at a portion contacting with the upper surface of the first solid electrolyte layer 12d, of the second spacer layer 12e intervening between the buffering space 22 and the first chamber 18. Finally, as also shown in FIG. 13, the third diffusion rate-determining section 30 is constructed as a communication hole 104 having a horizontal length longer than a vertical length formed at a portion contacting with the upper surface of the first solid electrolyte layer 12d, of the second spacer layer 12e intervening between the first chamber 18 and the second chamber 20. The gas sensor 10B is different from the gas sensor 10A according to the first embodiment in the foregoing points.

The communication hole 100 for constructing the first diffusion rate-determining section 26 and the communication hole 102 for constructing the second diffusion rate-determining section 28 are arranged in the following positional relationship. That is, when viewed on projection planes opposing to the gas-introducing direction, the communication hole 100 for constructing the first diffusion rate-determining section 26 is not overlapped with the communication hole 102 for constructing the second diffusion rate-determining section 28. In other words, they are formed such that the input into the buffering space 22 and the output therefrom are not aligned on a straight line. Of course, the communication holes 100, 102 may be positionally arranged to partially overlap with each other, or they may be arranged to make coincidence with each other. Further, a porous member such as alumina may be embedded in the communication hole 100 and/or the communication hole 102.

In the embodiment shown in FIGS. 9, 10, and 13, the communication hole 104 for constructing the third diffusion rate-determining section 30 is formed to make contact with the upper surface of the first solid electrolyte layer 12$d$. Alternatively, the communication hole 104 may be formed to make contact with the lower surface of the second solid electrolyte layer 12$f$.

When the gas sensor 10B according to the second embodiment is used, the oxygen suddenly enters the sensor element 14 via the gas-introducing port 24 due to the exhaust gas pressure pulsation in the external space. However, the oxygen from the external space does not directly enter the first chamber 18, but it enters the buffering space 22 disposed at the upstream thereof. That is, the sudden change in oxygen concentration, which is caused by the exhaust gas pressure pulsation, is counteracted by the buffering space 22. Thus, the influence of the exhaust gas pressure pulsation on the first chamber 18 is in an almost negligible degree.

As a result, the oxygen-pumping amount effected by the main pumping cell 44 in the first chamber 18 is well correlated with the oxygen concentration in the measurement gas, and it is possible to improve the measurement accuracy obtained by using the measuring pumping cell 64. Simultaneously, the first chamber 18 can be commonly used, for example, as a sensor for determining the air-fuel ratio.

An illustrative experiment (conveniently referred to as "third illustrative experiment") will now be described. The third illustrative experiment relates to Working Example 2 and Comparative Example, in order to plot values of the pumping current Ip1 flowing through the main pumping cell 44 when the concentration of oxygen contained in the measurement gas was changed. Obtained results are shown in FIG. 14A (Comparative Example) and FIG. 14B (Working Example 2).

Comparative Example was arranged in the same manner as the gas sensor used in the first and second illustrative experiments described above. Working Example 2 was arranged in the same manner as the gas sensor 10B according to the second embodiment.

Figure 14A:
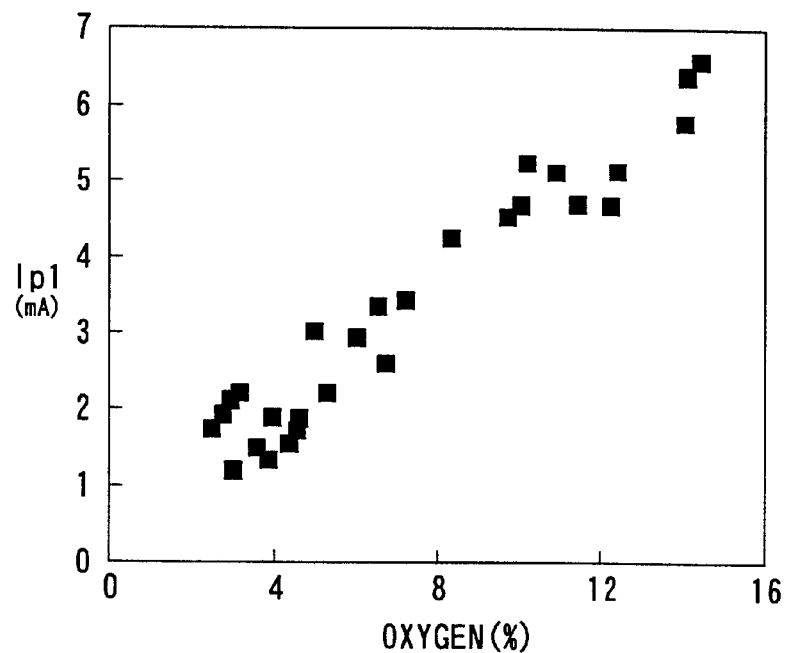
FIG. 14A shows a characteristic illustrating a result of a third illustrative experiment to observe the value of the pumping current flowing through a main pumping cell, obtained when the concentration of oxygen contained in the measurement gas is changed for a gas sensor concerning Comparative Example.

According to the results of the experiment, the following fact is understood for Comparative Example as shown in FIG. 14A. That is, the value of the pumping current Ip1 involves large dispersion even when the oxygen concentration is identical, and the correlation between the oxygen concentration and the pumping current Ip1 tends to disappear. Therefore, the detection current Ip2 also involves dispersion, and the measurement accuracy for NOx is deteriorated. This results from the fact that the first chamber 18 is directly affected by the influence caused by the exhaust gas pressure pulsation in the external space.

Figure 14B:
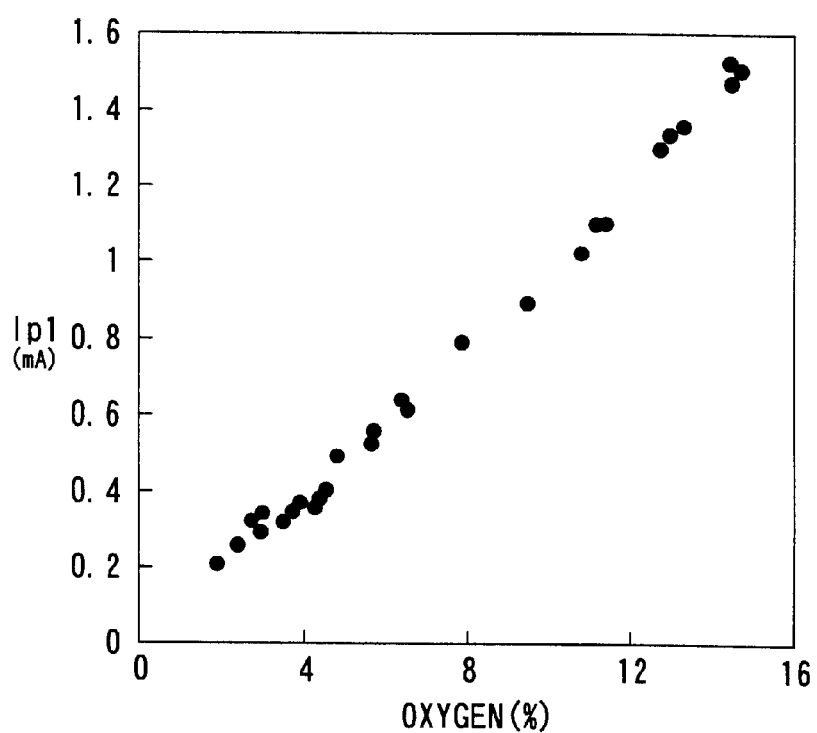
FIG. 14B shows a characteristic illustrating a result of the third illustrative experiment, obtained for a gas sensor concerning Working Example 2.

On the contrary, the following fact is understood for Working Example 2 as shown in FIG. 14B. That is, the value of the pumping current Ip1 is well correlated with the oxygen concentration. As a result, the detection current Ip2 hardly involves dispersion. This results from the fact that the presence of the buffering space 22 counteracts almost all influences which would be otherwise caused by the exhaust gas pressure pulsation in the external space.

Next, a modified embodiment 10B$a$ of the gas sensor 10B according to the second embodiment will be explained with reference to FIG. 15. Components or parts corresponding to those shown in FIG. 9 are designated by the same reference numerals, duplicate explanation of which will be omitted.

Figure 15:
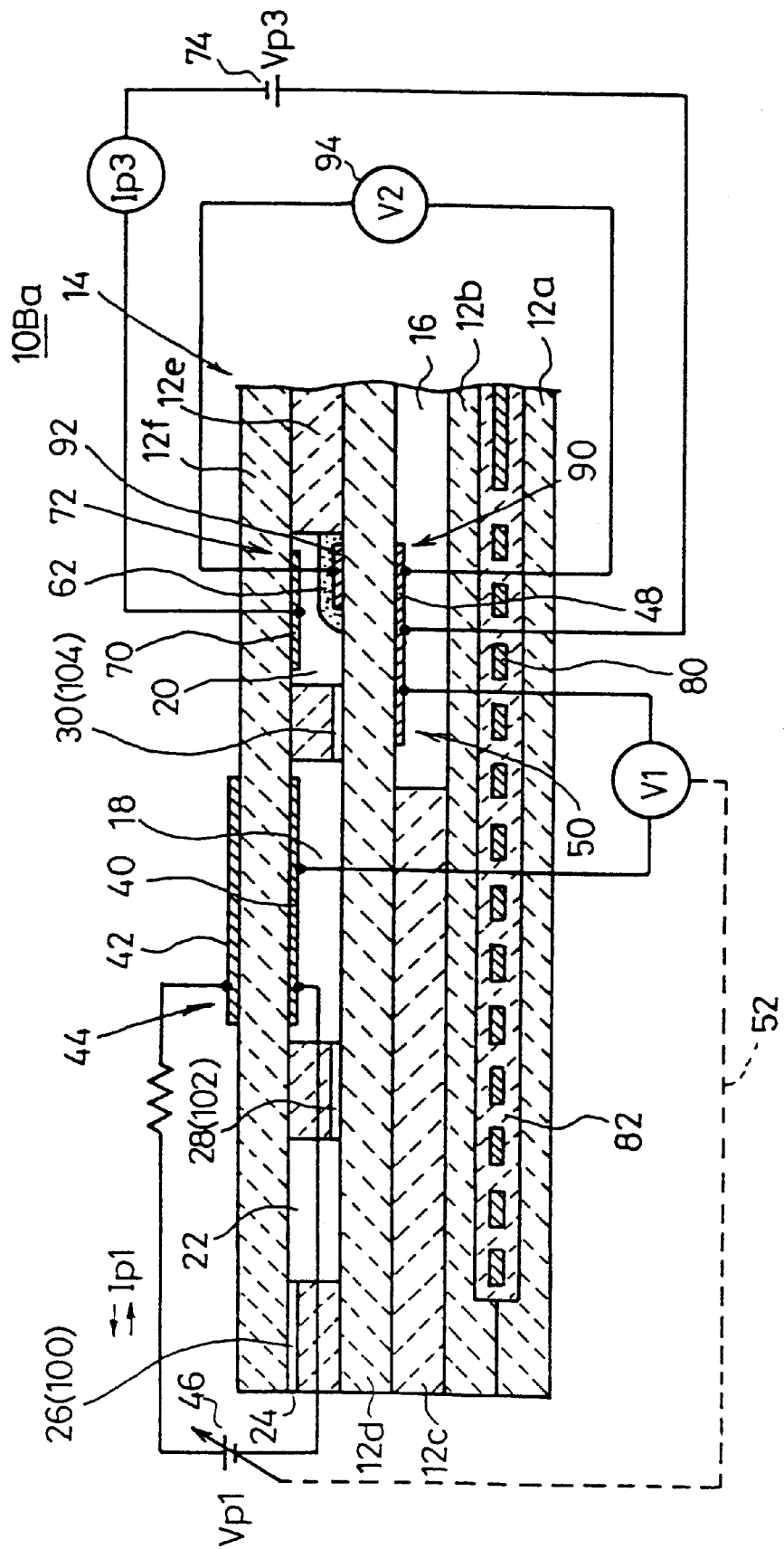
FIG. 15 shows a sectional view illustrating a modified embodiment of the gas sensor according to the second embodiment.

As shown in FIG. 15, a gas sensor 10B$a$ according to the modified embodiment is constructed in approximately the same manner as the gas sensor 10B according to the second embodiment (see FIG. 9). However, the former is different from the latter in that a measuring oxygen partial pressure-detecting cell 90 is provided in place of the measuring pumping cell 64.

In this embodiment, an electromotive force (electromotive force of an oxygen concentration cell) V2 corresponding to the difference in oxygen concentration between the atmosphere around the detecting electrode 92 and the atmosphere around the reference electrode 48 is generated between the reference electrode 48 and the detecting electrode 92 of the measuring oxygen partial pressure-detecting cell 90, in the same manner as in the modified embodiment 10A$a$ (see FIG. 8) of the gas sensor 10A according to the first embodiment.

Therefore, the partial pressure of oxygen in the atmosphere around the detecting electrode 92, in other words, the partial pressure of oxygen defined by oxygen produced by reduction or decomposition of the measurement gas component (NOx) is detected as a voltage value by measuring the electromotive force (voltage V2) generated between the detecting electrode 92 and the reference electrode 48 by using a voltmeter 94.

The gas sensor 10B$a$ according to the modified embodiment also includes the buffering space 22 disposed between the gas-introducing port 24 and the first chamber 18. Therefore, the sudden change in oxygen concentration due to the exhaust gas pressure pulsation is counteracted by the buffering space 22, and the influence of the exhaust gas pressure pulsation on the first chamber 18 is in an almost negligible degree.

As a result, the oxygen-pumping amount effected by the main pumping cell 44 for the first chamber 18 is well correlated with the oxygen concentration in the measurement gas, and it is possible to improve the measurement accuracy obtained by using the measuring oxygen partial pressure-detecting cell 90, in the same manner as in the modified embodiment 10A$a$ of the gas sensor according to the first embodiment. Simultaneously, the first chamber 18 can be commonly used, for example, as a sensor for determining the air-fuel ratio.

Consideration will now be made for the relationship between the pumping current Ip1 flowing through the main pumping cell 44 and the volume of the buffering space 22.

It is considered that the volume of the preferable buffering space 22 has any relationship with the pumping current Ip1 flowing through the main pumping cell 44.

Concerning the gas sensor 10B (see FIG. 9) according to the second embodiment, it is assumed that the respective gas diffusion resistances of the first and second diffusion rate-determining sections 26, 28 are D1 and D2, the respective cross-sectional areas of the communication hole 100 having the longer horizontal length for constructing the first diffusion rate-determining section 26 and the communication hole 102 having the longer horizontal length for constructing the second diffusion rate-determining section 28 are S1 and S2, and the lengths of the communication holes 100, 102 along the gas-introducing direction are L1 and L2 respectively. On this assumption, the following expressions are given.

D1=L1/S1
D2=L2/S2

The pumping current Ip1 flowing through the main pumping cell 44 is approximated by the following expression.

$$Ip1 \sim (4F/RT) = D = (S/L) = (POe-POd)$$

In the expression, F represents the Faraday constant (A•sec), R represents the gas constant (=82.05cm$^3$•atm/ K•mol), T represents the absolute temperature (K), D represents the gas diffusion coefficient of oxygen (=1.68cm$^2$/ sec), S/L represents the reciprocal of combined value of the diffusion resistances D1 and D2, and (POe–POd) represents the difference between the oxygen concentration of the measurement gas in the external space and the oxygen concentration in the first chamber 18.

The gas sensors 10A, 10B according to the first and second embodiments (including the respective modified embodiments 10Aa, 10Ba) are constructed such that the volume of the buffering space 22 is determined depending on the magnitude of the combined value L/S of the diffusion resistances D1, D2.

For example, both of the gas sensors 10A, 10B according to the first and second embodiments are formed such that the first diffusion rate-determining section 26 and the second diffusion rate-determining section 28 are provided in series. Accordingly, the combined value of the respective diffusion resistances D1, D2 is D1+D2. Therefore, the volume of the buffering space 22 has a size corresponding to D1+D2.

Especially, in the gas sensors 10A, 10B according to the first and second embodiments, the diffusion resistance D1 of the first diffusion rate-determining section 26 is set to be larger than the diffusion resistance D2 of the second diffusion rate-determining section 28.

Therefore, in the gas sensors 10A, 10B according to the first and second embodiments (including the respective modified embodiments 10Aa, 10Ba), the sudden invasion of the measurement gas into the buffering space 22, which would be caused by the exhaust gas pressure pulsation in the external space, can be suppressed more effectively. Thus, it is possible to exhibit, in a more effective manner, the effect of the buffering space 22 to eliminate the influence of the exhaust gas pressure pulsation on the first chamber 18.

Although not shown in the drawings, the communication hole 100 for constructing the first diffusion rate-determining section 26 and the communication hole 102 for constructing the second diffusion rate-determining section 28 may be formed at positions opposite to those adopted in the second embodiment (see FIG. 9). That is, the communication hole 100 may be formed at a position near to the first solid electrolyte layer 12d, and the communication hole 102 may be formed at a position near to the second solid electrolyte layer 12f.

In this case, the communication hole 104 for constructing the third diffusion rate-determining section 30 may be formed to make contact with the lower surface of the second solid electrolyte layer 12f. Alternatively, although not shown, the communication hole 104 may be formed to make contact with the upper surface of the first solid electrolyte layer 12d.

Next, two modified embodiments will be explained with reference to FIGS. 16 to 19 concerning the arrangement of the first and second diffusion rate-determining sections 26, 28 of the gas sensor 10B according to the second embodiment (including the modified embodiment 10Ba).

Figure 16:
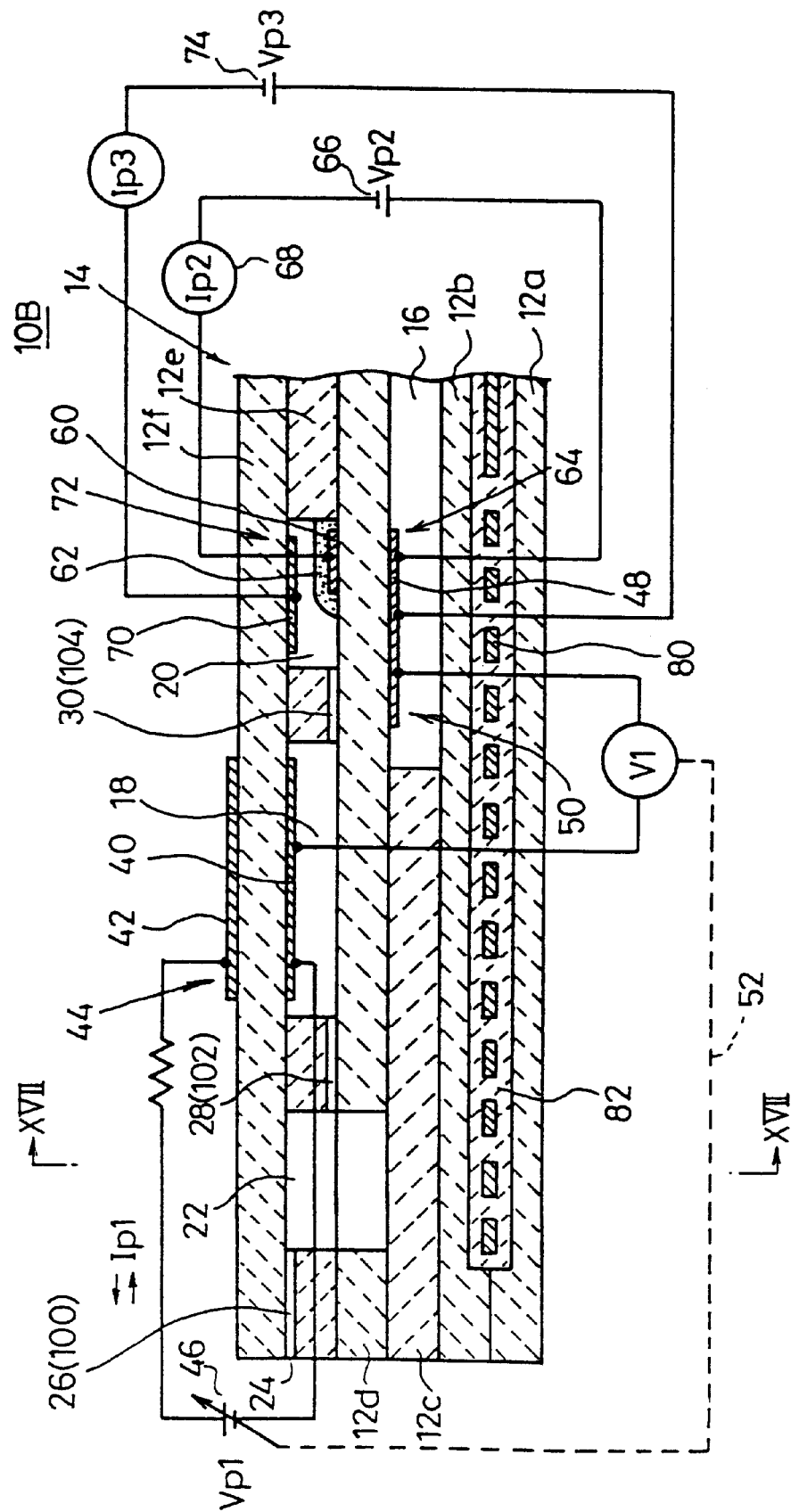
FIG. 16 shows a sectional view illustrating an arrangement of a first modified embodiment concerning the diffusion rate-determining section of the gas sensor according to the second embodiment.
Figure 17:
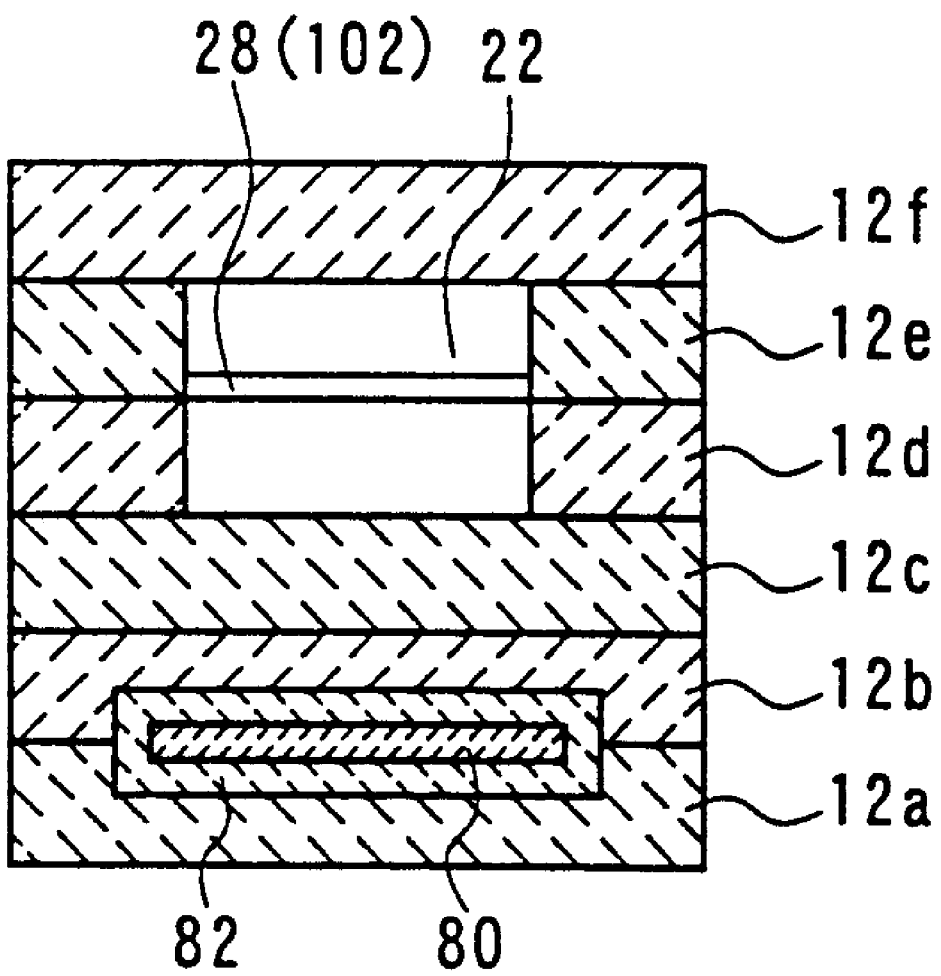
FIG. 17 shows a sectional view taken along a line XVII—XVII shown in FIG. 16.

At first, the first modified embodiment is constructed as follows as shown in FIGS. 16 and 17, based on the gas sensor 10B according to the second embodiment. That is, a portion of the first solid electrolyte layer 12d, which contacts with the buffering space 22, is removed to increase the volume of the buffering space 22 twice. Accordingly, it is possible to further reduce the influence of the exhaust gas pressure pulsation on the first chamber 18.

In this embodiment, the communication hole 100 for constructing the first diffusion rate-determining section 26 is formed at the position in the second spacer layer 12e near to the second solid electrolyte layer 12f.

Alternatively, the communication hole 100 may be formed at a position in the second spacer layer 12e near to the first solid electrolyte layer 12d. Further alternatively, the communication hole 100 may be formed at a position in the first solid electrolyte layer 12d near to the second spacer layer 12e, or the communication hole 100 may be formed at a position in the first solid electrolyte layer 12d near to the first spacer layer 12c.

Figure 18:
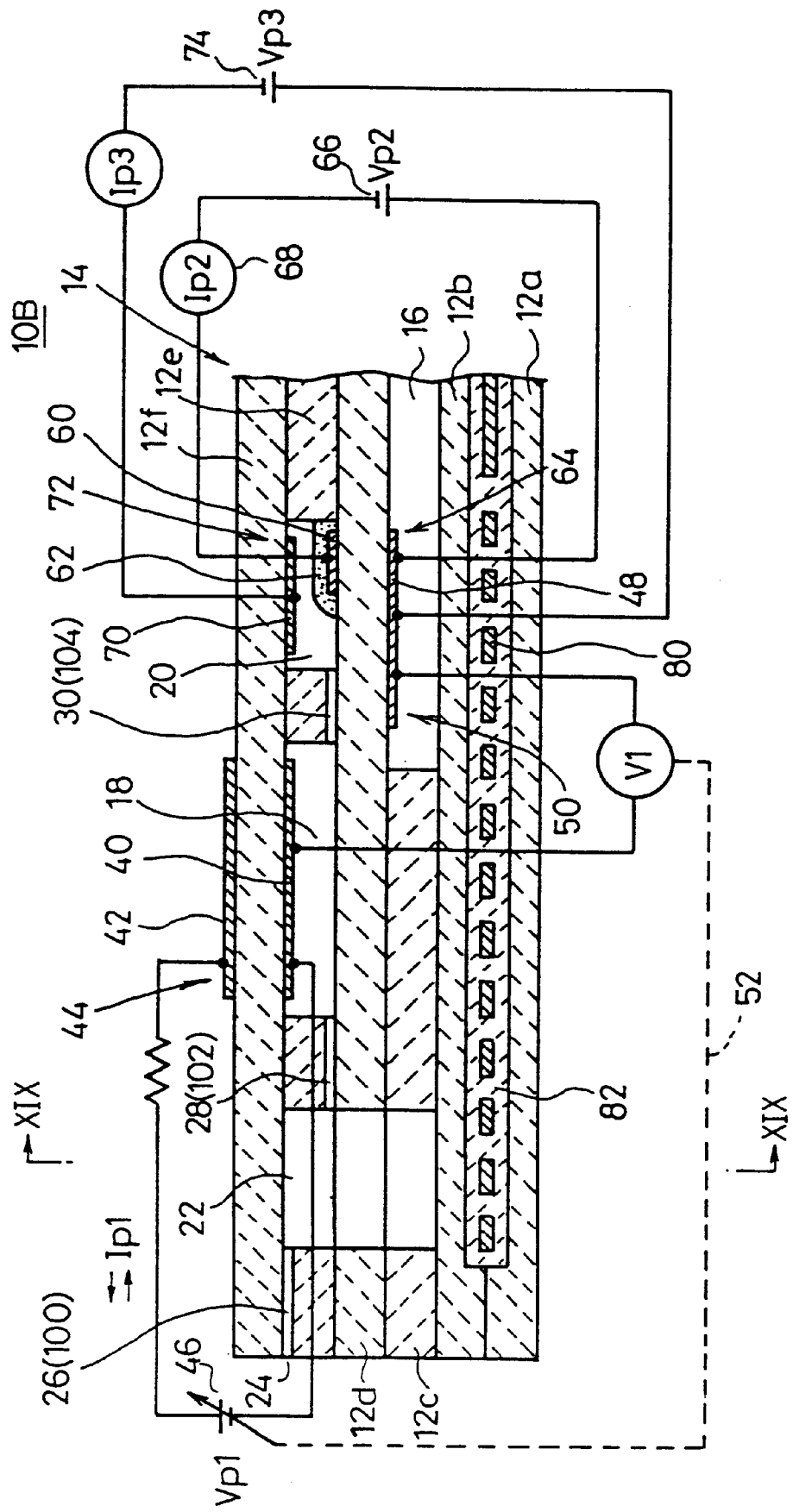
FIG. 18 shows a sectional view illustrating an arrangement of a second modified embodiment concerning the diffusion rate-determining section of the gas sensor according to the second embodiment.
Figure 19:
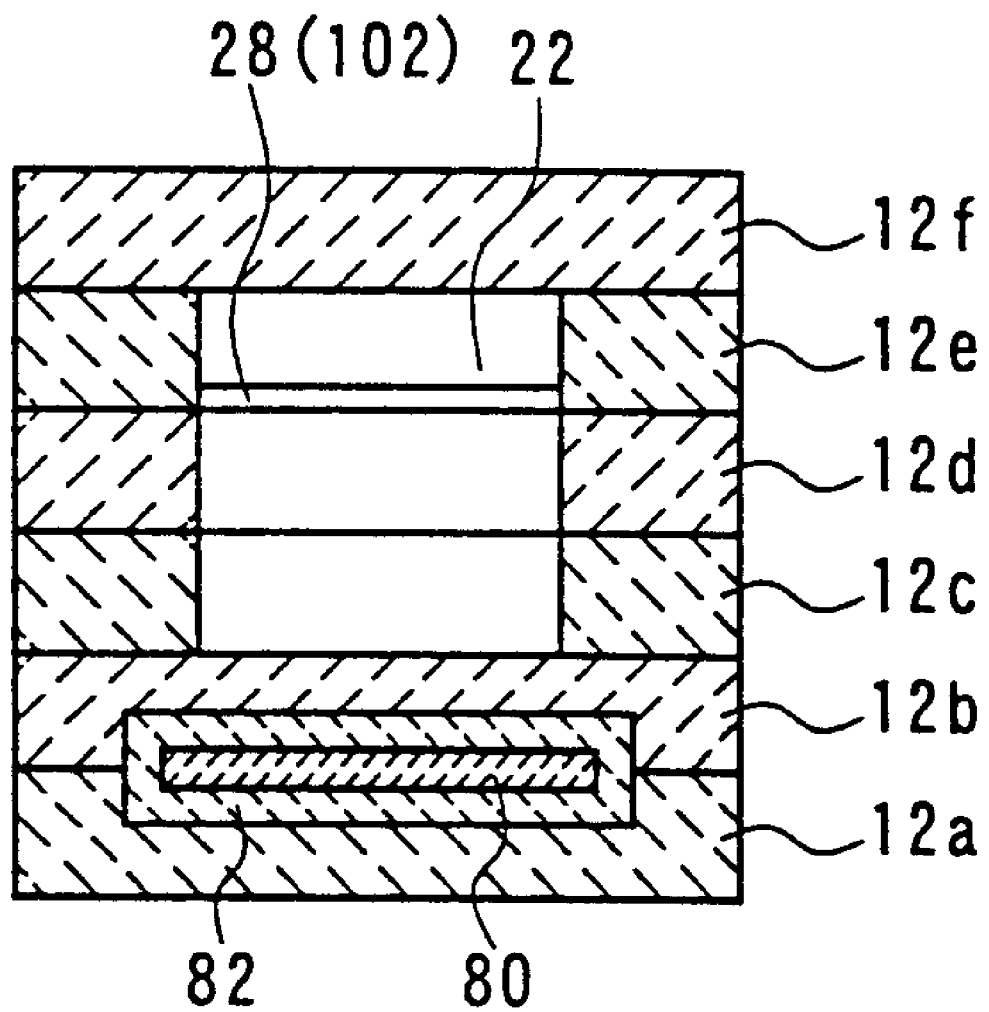
FIG. 19 shows a sectional view taken along a line XIX—XIX shown in FIG. 18.

Secondly, the second modified embodiment is constructed as follows as shown in FIGS. 18 and 19, based on the gas sensor 10B according to the second embodiment. That is, a portion of the first solid electrolyte layer 12d, which contacts with the buffering space 22, is removed, and a part of the underlying first spacer layer 12c is further removed to increase the volume of the buffering space 22 by three times. Accordingly, it is possible to further reduce the influence of the exhaust gas pressure pulsation on the first chamber 18, as compared with the first modified embodiment described above (see FIG. 16).

In the embodiment shown in FIG. 18, the communication hole 100 for constructing the first diffusion rate-determining section 26 is formed at the position in the second spacer layer 12e near to the second solid electrolyte layer 12f. Alternatively, the communication hole 100 may be formed at a position in the second spacer layer 12e near to the first solid electrolyte layer 12d.

Further alternatively, the communication hole 100 may be formed at a position in the first solid electrolyte layer 12d near to the second spacer layer 12e, or the communication hole 100 may be formed at a position in the first solid electrolyte layer 12d near to the first spacer layer 12c. Further alternatively, the communication hole 100 may be formed at a position in the first spacer layer 12c near to the first solid electrolyte layer 12d, or the communication hole 100 may be formed at a position in the first spacer layer 12c near to the second substrate layer 12b.

Next, a gas sensor 10C according to the third embodiment will be explained with reference to FIGS. 20 to 24. Components or parts corresponding to those shown in FIG. 9 are designated by the same reference numerals, duplicate explanation of which will be omitted.

Figure 20:
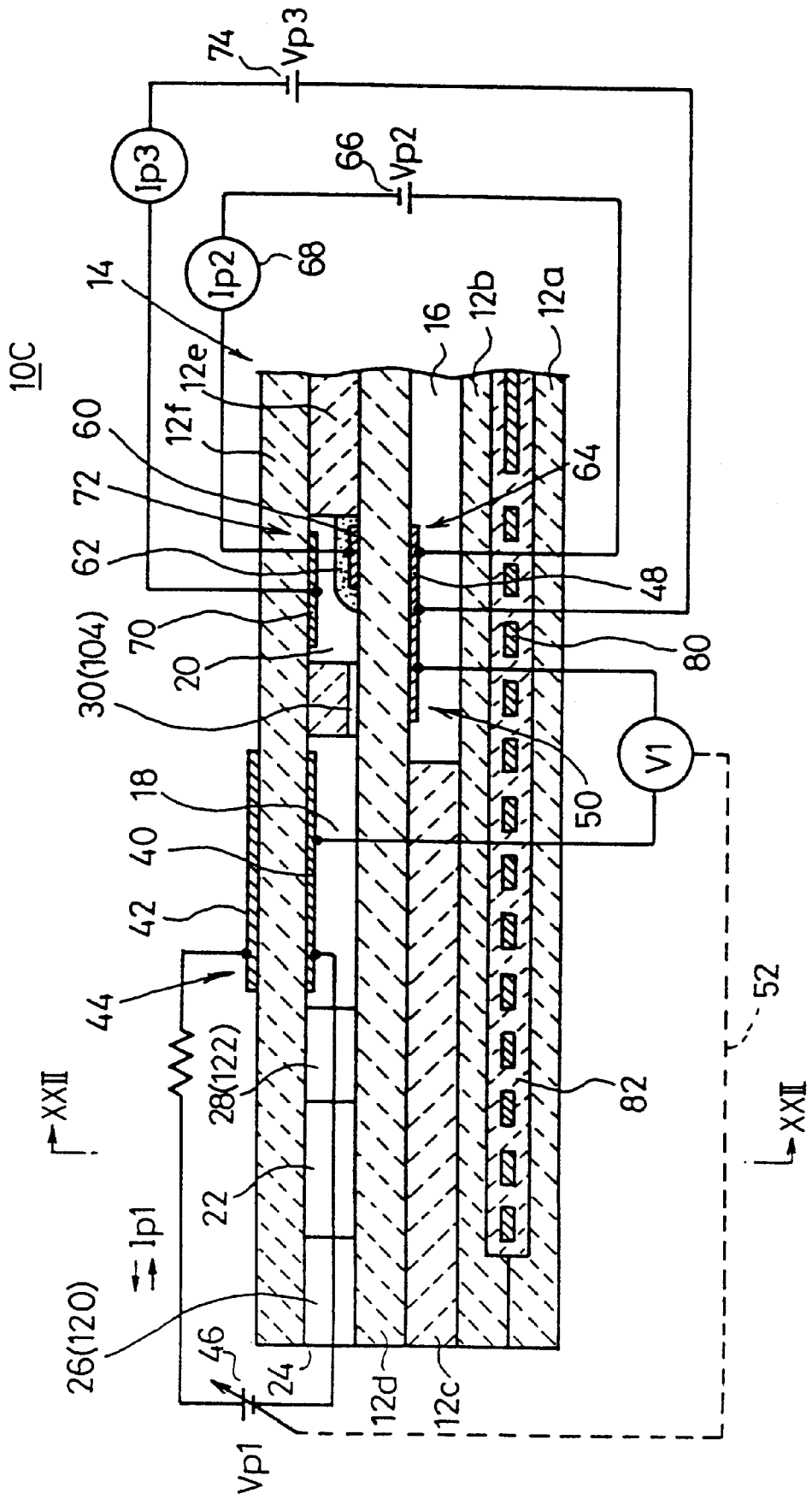
FIG. 20 shows a sectional view illustrating an arrangement of a gas sensor according to a third embodiment.
Figure 21:
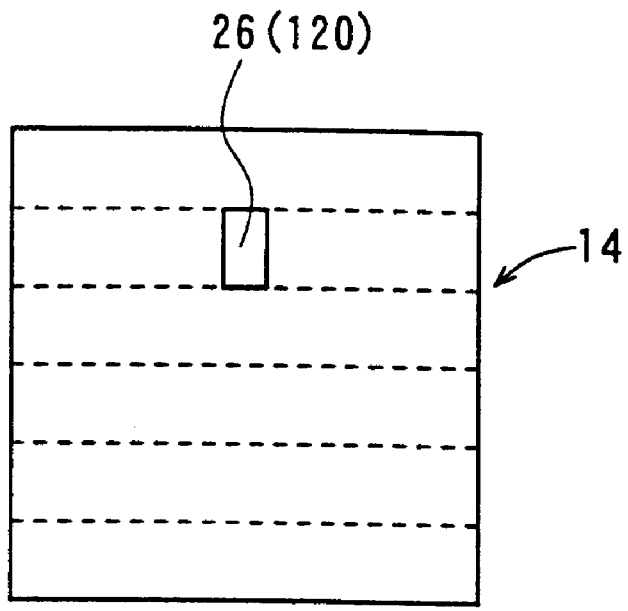
FIG. 21 shows a front view illustrating the gas sensor according to the third embodiment.
Figure 22:
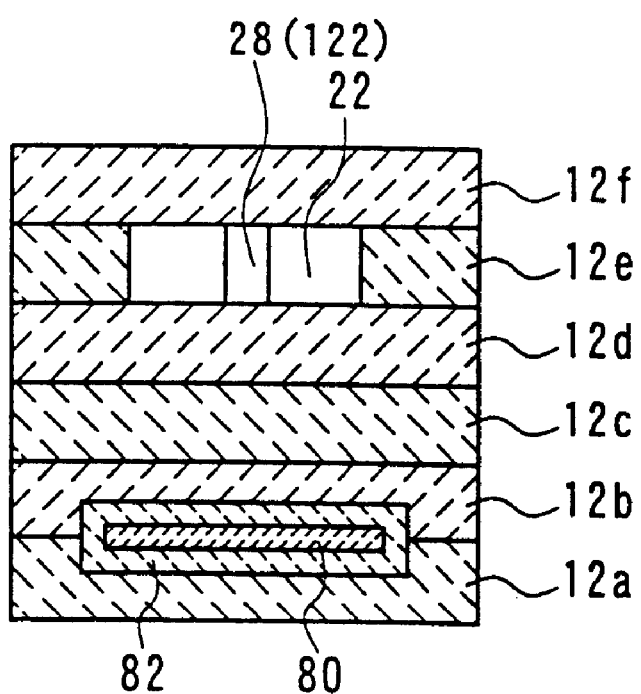
FIG. 22 shows a sectional view taken along a line XXII—XXII shown in FIG. 20.

As shown in FIGS. 20 to 22, the gas sensor 10C according to the third embodiment is constructed in approximately the same manner as the gas sensor 10B according to the second embodiment (see FIG. 9). However, the former is different from the latter in that the first and second diffusion rate-determining sections 26, 28 are slits 120, 122 each having a vertical length longer than a horizontal length.

The embodiment shown in FIGS. 21 and 22 is illustrative of a case in which the slit 120 for constructing the first diffusion rate-determining section 26 and the slit 122 for constructing the second diffusion rate-determining section 28 are formed at positions approximately identical with each other, as viewed on projection planes opposing to the gas-introducing direction.

Of course, the slits 120, 122 may be positionally arranged to partially overlap with each other, or they may be arranged to make no overlap with each other. Further, a porous member such as alumina may be embedded in the slit 120 and/or the slit 122.

Figure 23:
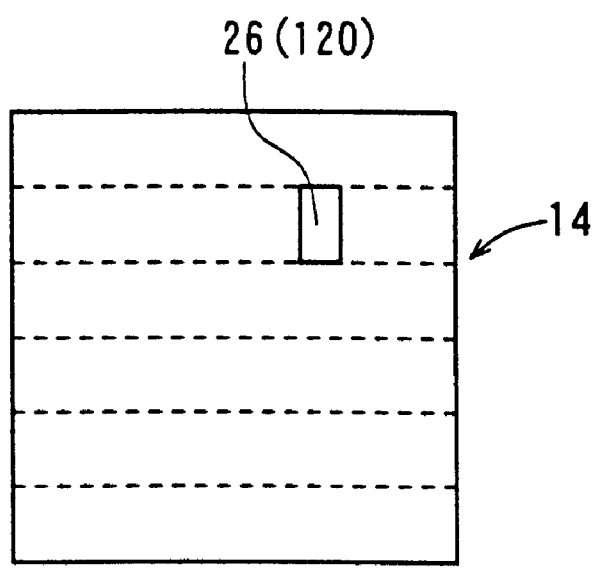
FIG. 23 shows a front view illustrating a modified embodiment of the gas sensor according to the third embodiment.
Figure 24:
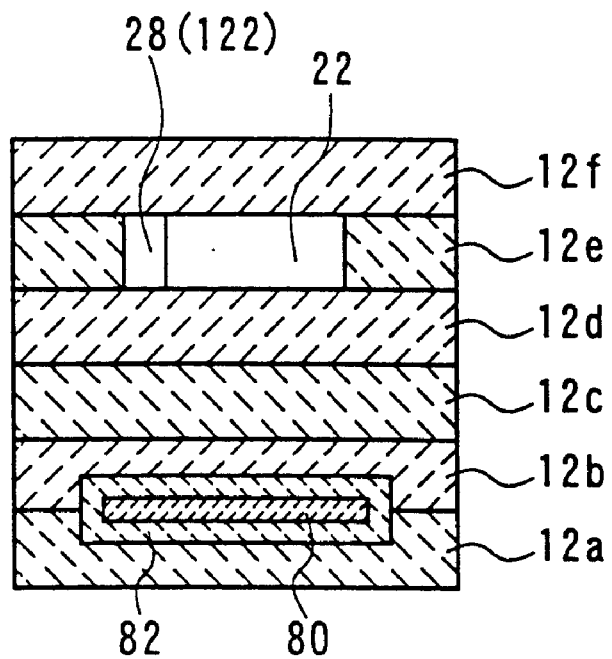
FIG. 24 shows a modified embodiment of the gas sensor according to the third embodiment, illustrating a sectional view taken along the same line as the line XXII—XXII shown in FIG. 20.

The arrangement may be realized, for example, as follows so that the slits 120, 122 are not overlapped with each other. That is, as shown in FIG. 23, the slit 120 having the longer vertical length for constructing the first diffusion rate-determining section 26 is formed, for example, at a position deviated toward the right side (or at a position deviated toward the left side), when the sensor element 14 is viewed from a position in front thereof, while as shown in FIG. 24, the slit 122 for constructing the second diffusion rate-determining section 28 is formed at a position deviated toward the left side (or at a position deviated toward the right side).

The gas sensor 10C according to the third embodiment may be also provided with the measuring oxygen partial pressure-detecting cell 90 in place of the measuring pumping cell 64 in the same manner as in the modified embodiment 10Ba (see FIG. 15) of the gas sensor 10B according to the second embodiment. Further, the gas sensor 10C according to the third embodiment may be constructed as follows in the same manner as in the first modified embodiment (see FIG. 16) and the second modified embodiment (see FIG. 18) of the gas sensor 10B according to the second embodiment. That is, a portion of the first solid electrolyte layer 12d contacting with the buffering space 22 may be removed to increase the volume of the buffering space 22 twice. Further, a portion of the first solid electrolyte layer 12d contacting with the buffering space 22 may be removed, and a part of the underlying first spacer layer 12c may be removed to increase the volume of the buffering space 22 by three times.

Also in these embodiments, the slit 120 for constructing the first diffusion rate-determining section 26 may be provided in the first solid electrolyte layer 12d. Especially, in the case of the gas sensor of the type in which the volume of the buffering space 22 is increased by three times (see FIG. 18), the slit 120 may be provided in the first spacer layer 12c.

Next, a gas sensor 10D according to the fourth embodiment will be explained with reference to FIGS. 25 to 27. Components or parts corresponding to those shown in FIG. 9 are designated by the same reference numerals, duplicate explanation of which will be omitted.

Figure 25:
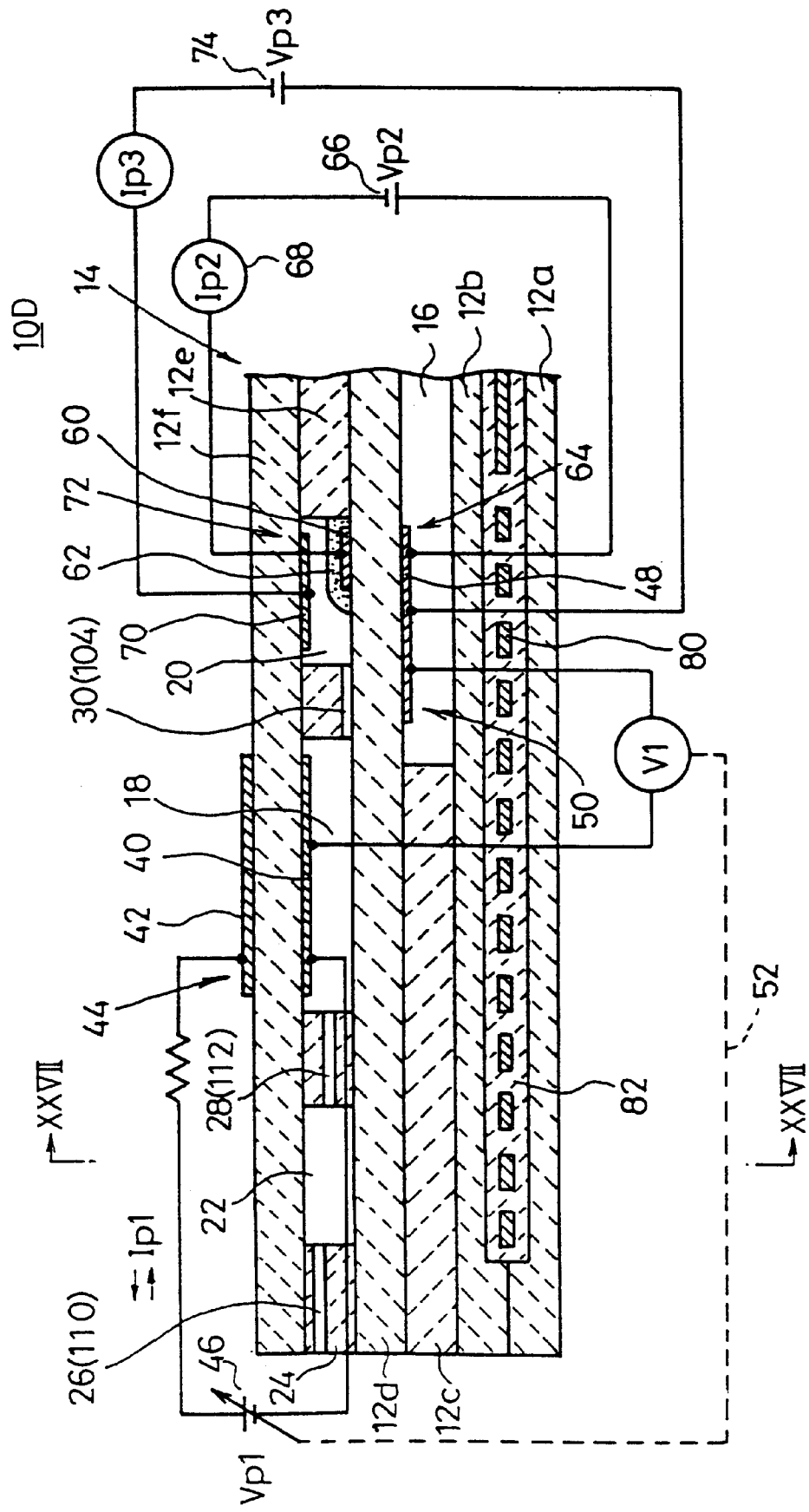
FIG. 25 shows a sectional view illustrating an arrangement of a gas sensor according to a fourth embodiment.
Figure 26:
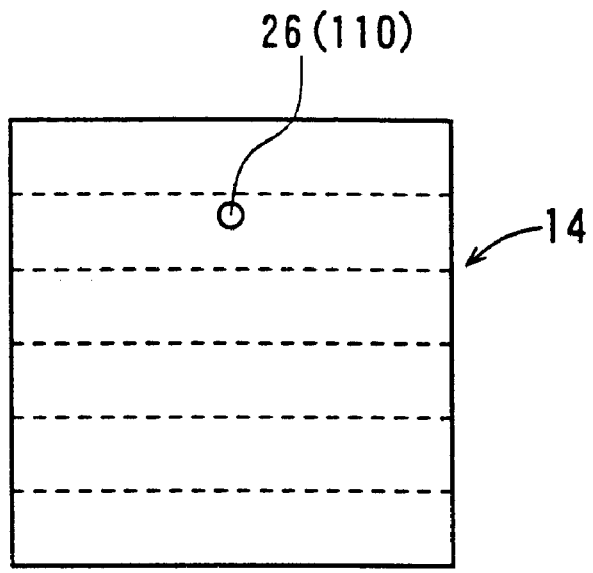
FIG. 26 shows a front view illustrating the gas sensor according to the fourth embodiment.
Figure 27:
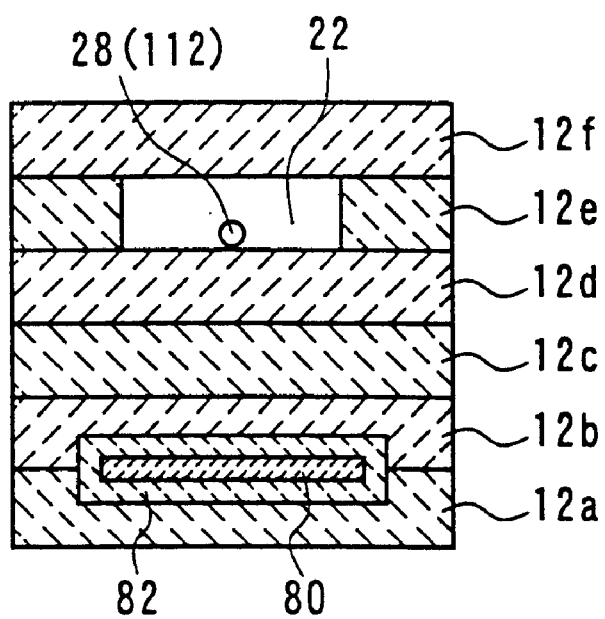
FIG. 27 shows a sectional view taken along a line XXVII—XXVII shown in FIG. 25.

As shown in FIGS. 25 to 27, the gas sensor 10D according to the fourth embodiment is constructed in approximately the same manner as the gas sensor 10B according to the second embodiment (see FIG. 9). However, the former is different from the latter in that the first and second diffusion rate-determining sections 26, 28 are small holes 110, 112 each having a substantially circular cross section.

In this embodiment, it is preferable that the small hole 110 for constructing the first diffusion rate-determining section 26 is not overlapped with the small hole 112 for constructing the second diffusion rate-determining section 28, when they are viewed on projection planes opposing to the gas-introducing direction. This arrangement may be realized, for example, as follows as shown in FIGS. 26 and 27. That is, the small hole 110 for constructing the first diffusion rate-determining section 26 is formed at a substantially central portion in the widthwise direction of the second spacer layer 12e, the portion being in the vicinity of the second solid electrolyte layer 12f disposed thereover. The small hole 112 for constructing the second diffusion rate-determining section 28 is formed at a substantially central portion in the widthwise direction of the second spacer layer 12e, the portion being in the vicinity of the first solid electrolyte layer 12d disposed thereunder.

Of course, the arrangement described above may be realized as follows. That is, the small hole 110 for constructing the first diffusion rate-determining section 26 is formed, for example, at a position deviated toward the right side, when the sensor element 14 is viewed from a position in front thereof, while the small hole 112 for constructing the second diffusion rate-determining section 28 is formed at a position deviated toward the left side.

The small holes 110, 112 may be positionally arranged to partially overlap with each other, or they may be arranged to make coincidence with each other. Further, a porous member such as alumina may be embedded in the small hole 110 and/or the small hole 112.

The gas sensor 10D according to the fourth embodiment may be also provided with the measuring oxygen partial pressure-detecting cell 90 in place of the measuring pumping cell 64 in the same manner as in the modified embodiment 10Ba (see FIG. 15) of the gas sensor 10B according to the second embodiment. Further, the gas sensor 10D according to the fourth embodiment may be constructed as follows in the same manner as in the first modified embodiment (see FIG. 16) and the second modified embodiment (see FIG. 18) of the gas sensor 10B according to the second embodiment. That is, a portion of the first solid electrolyte layer 12d contacting with the buffering space 22 may be removed to increase the volume of the buffering space 22 twice. Further, a portion of the first solid electrolyte layer 12d contacting with the buffering space 22 may be removed, and a part of the underlying first spacer layer 12c may be removed to increase the volume of the buffering space 22 by three times.

Also in these embodiments, the small hole 110 for constructing the first diffusion rate-determining section 26 may be provided in the first solid electrolyte layer 12d. Especially, in the case of the gas sensor of the type in which the volume of the buffering space 22 is increased by three times (see FIG. 18), the small hole 110 may be provided in the first spacer layer 12c.

Next, a gas sensor 10E according to the fifth embodiment will be explained with reference to FIGS. 28 and 29. Components or parts corresponding to those shown in FIG. 9 are designated by the same reference numerals, duplicate explanation of which will be omitted.

Figure 28:
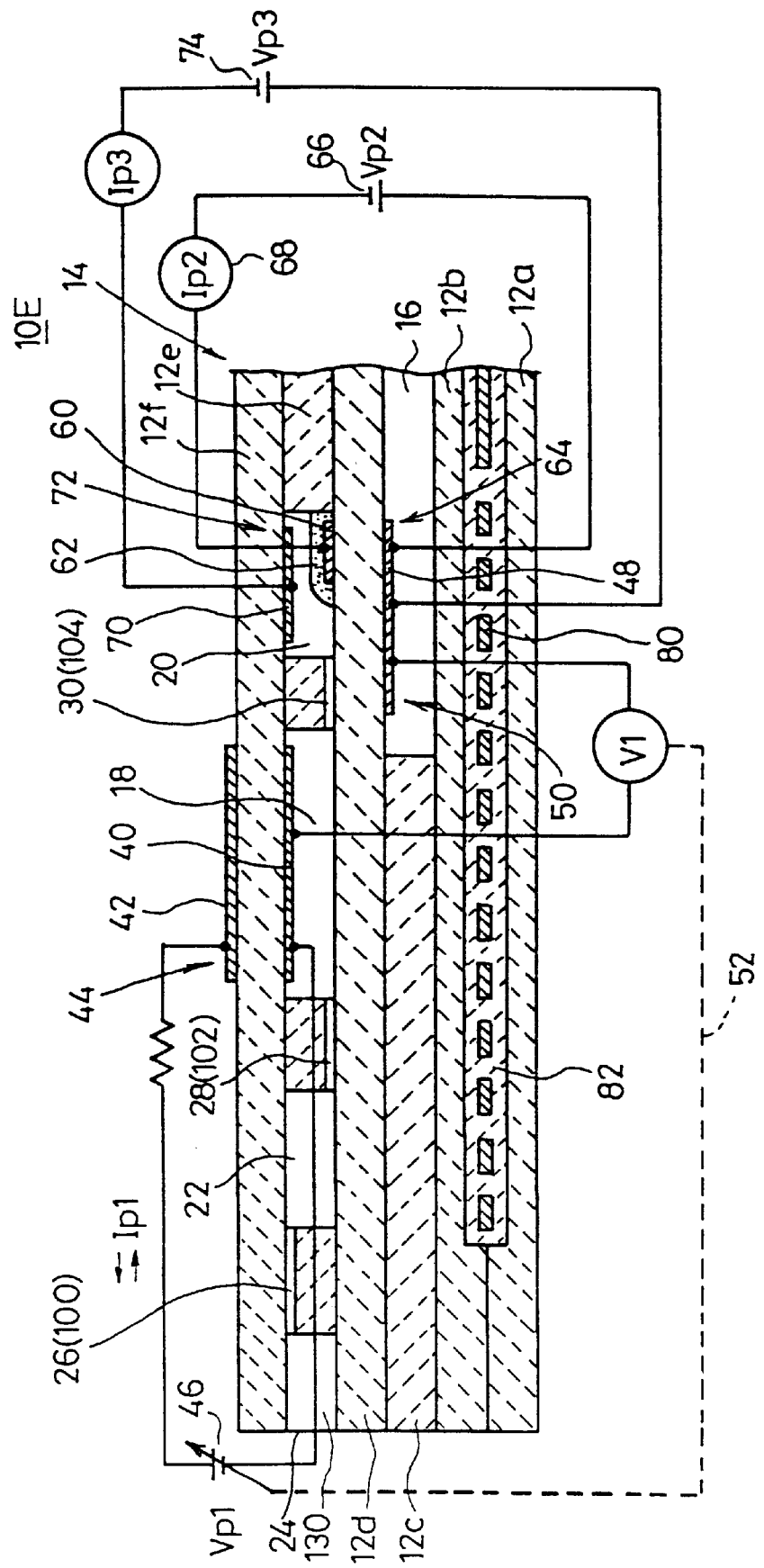
FIG. 28 shows a sectional view illustrating an arrangement of a gas sensor according to a fifth embodiment.

As shown in FIG. 28, the gas sensor 10E according to the fifth embodiment is constructed in approximately the same manner as the gas sensor 10B according to the second embodiment (see FIG. 9). However, the former is different from the latter in that a space section 130 is formed between the first diffusion rate-determining section 26 and the gas-introducing port 24 formed at the front end of the second spacer layer 12e. The space section 130 functions as a clogging-preventive section 130 for avoiding clogging of particles (for example, soot and oil combustion waste) produced in the measurement gas in the external space at the inlet of the buffering space 22 or in the vicinity thereof. Accordingly, it is possible to measure the NOx component more accurately by using the measuring pumping cell 64.

The gas sensor 10E according to the fifth embodiment may be also provided with the measuring oxygen partial pressure-detecting cell 90 in place of the measuring pumping cell 64 in the same manner as in the modified embodiment 10Ba (see FIG. 15) of the gas sensor 10B according to the second embodiment. Further, the gas sensor 10E according to the fifth embodiment may be constructed as follows in the same manner as in the first modified embodiment (see FIG. 16) and the second modified embodiment (see FIG. 18) of the gas sensor 10B according to the second embodiment. That is, a portion of the first solid electrolyte layer 12d contacting with the buffering space 22 may be removed to increase the volume of the buffering space 22 twice. Further, a portion of the first solid electrolyte layer 12d contacting with the buffering space 22 may be removed, and a part of the underlying first spacer layer 12c may be removed to increase the volume of the buffering space 22 by three times.

Also in these embodiments, the communication hole 100 for constructing the first diffusion rate-determining section 26 may be formed at a position in the second spacer layer 12e near to the first solid electrolyte layer 12d. Alternatively, the communication hole 100 may be formed at a position in the first solid electrolyte layer 12d near to the second spacer layer 12e, or the communication hole 100 may be formed at a position in the first solid electrolyte layer 12d near to the first spacer layer 12c. Further alternatively, the communication hole 100 may be formed at a position in the first spacer layer 12c near to the first solid electrolyte layer 12d, or the communication hole 100 may be formed at a position in the first spacer layer 12c near to the second substrate layer 12b.

Figure 29:
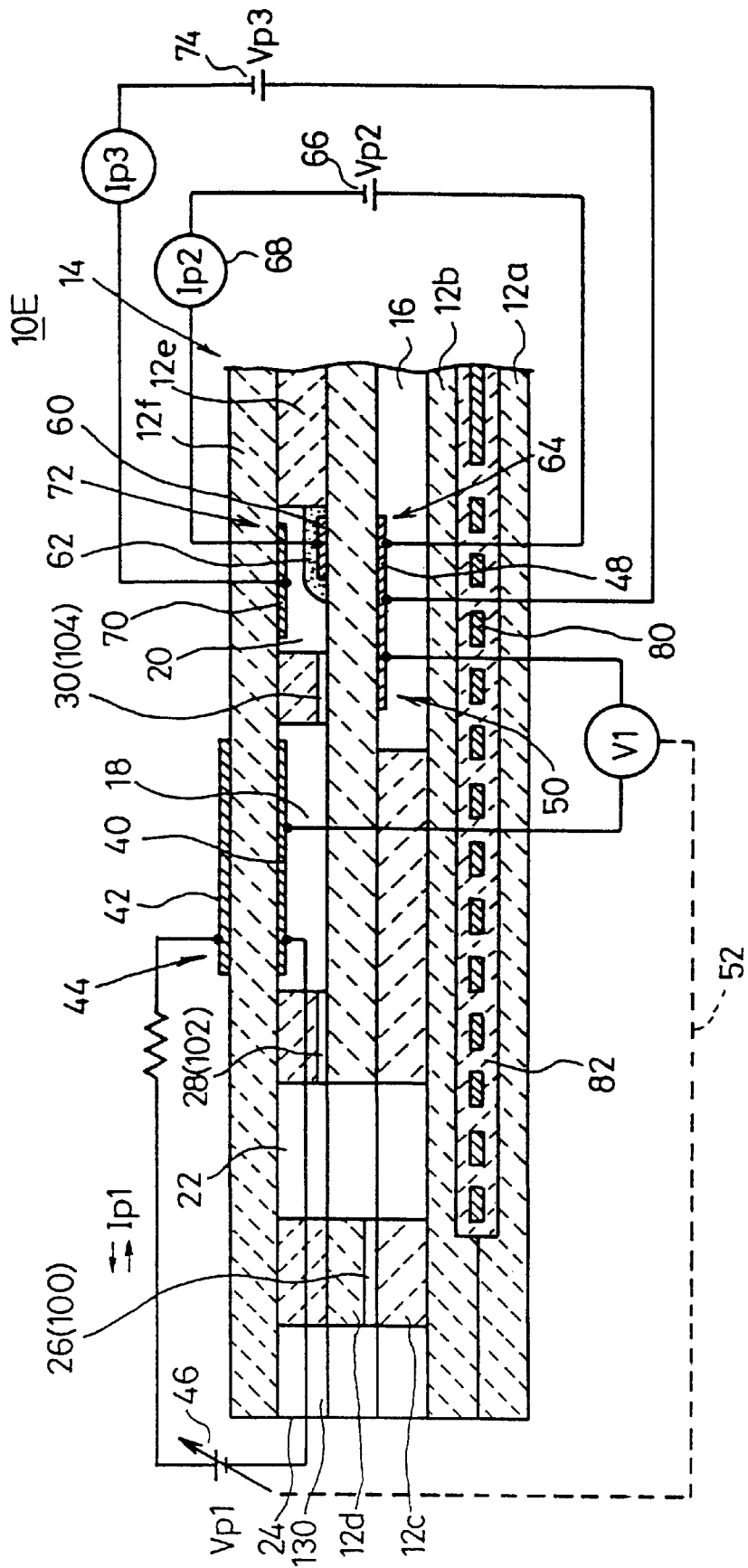
FIG. 29 shows a sectional view illustrating an arrangement of a modified embodiment of the gas sensor according to the fifth embodiment.

Especially, when the same arrangement is adopted as that of the gas sensor of the type in which the volume of the buffering space 22 is increased by three times (see FIG. 18), for example, the opening of the clogging-preventive section 130 may be continuously formed to range over the first spacer layer 12c, the first solid electrolyte layer 12d, and the second spacer layer 12e as shown in FIG. 29.

Figure 30:
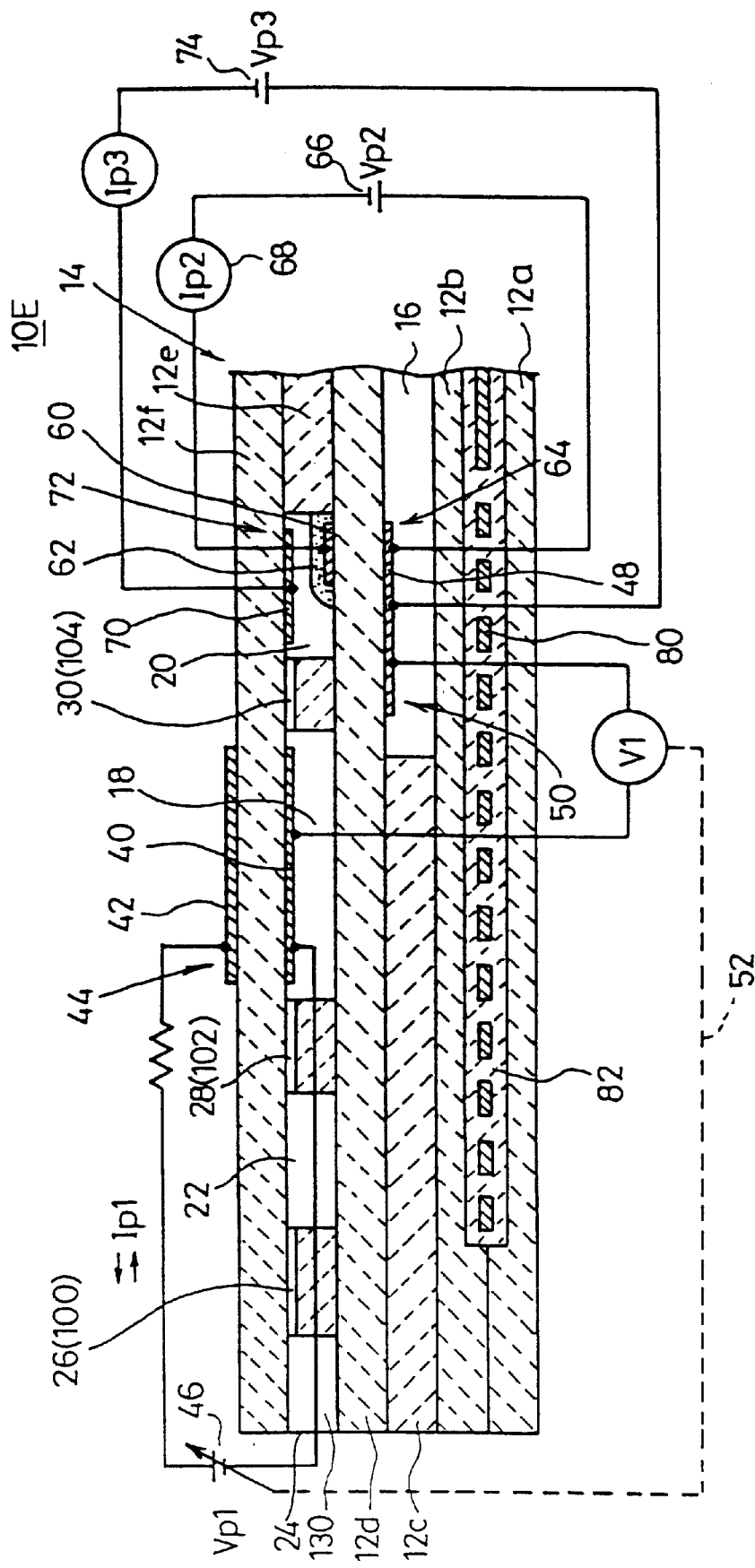
FIG. 30 shows a sectional view illustrating an arrangement of a first modified embodiment concerning the diffusion rate-determining section of the gas sensor according to the fifth embodiment.

In the gas sensor 10E according to the fifth embodiment, the communication hole 102 for constructing the second diffusion rate-determining section 28 and the communication hole 104 for constructing the third diffusion rate-determining section 30 are formed at each position in the second spacer layer 12e near to the first solid electrolyte layer 12d. Alternatively, as shown in FIG. 30, the communication holes 102 and 104 may be formed at each position in the second spacer layer 12e near to the second solid electrolyte layer 12f.

Figure 31:
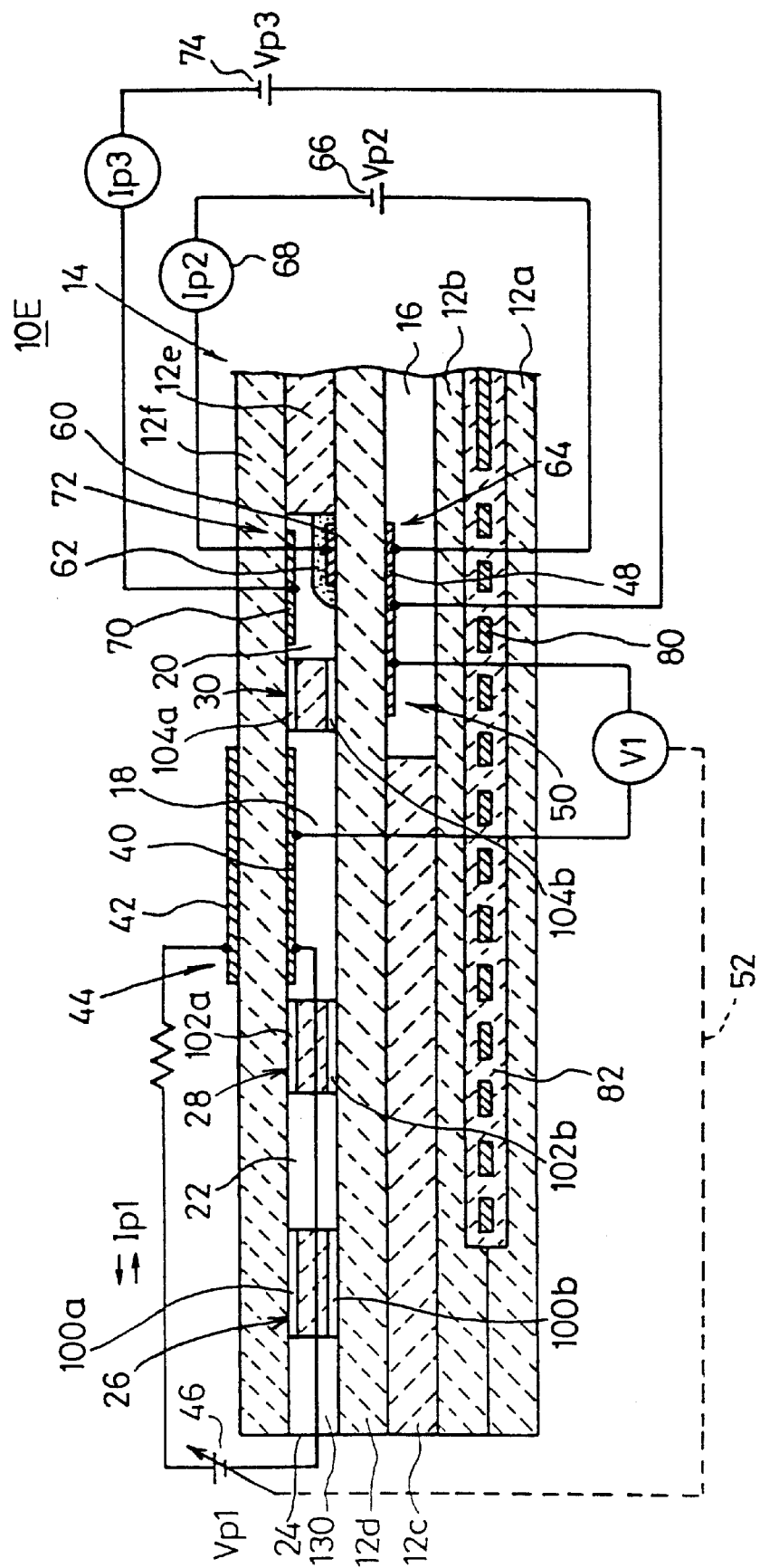
FIG. 31 shows a sectional view illustrating an arrangement of a second modified embodiment concerning the diffusion rate-determining section of the gas sensor according to the fifth embodiment.

As shown in FIG. 31, the first diffusion rate-determining section 26 may be constructed as a communication hole 10a formed at a portion contacting with the lower surface of the second solid electrolyte layer 12f and a communication hole 100b formed at a portion contacting with the upper surface of the first solid electrolyte layer 12d.

Similarly, the second diffusion rate-determining section 28 may be constructed as a communication hole 102a formed at a portion contacting with the lower surface of the second solid electrolyte layer 12f and a communication hole 102b formed at a portion contacting with the upper surface of the first solid electrolyte layer 12d. The third diffusion rate-determining section 30 may be constructed as a communication hole 104a formed at a portion contacting with the lower surface of the second solid electrolyte layer 12f and a communication hole 104b formed at a portion contacting with the upper surface of the first solid electrolyte layer 12d.

The gas sensors 10A to 10E according to the first to fifth embodiments described above (including the respective modified embodiments 10Aa, 10Ba) are directed to NOx as the measurement gas component to be measured. However, the present invention is also effectively applicable to the measurement of bound oxygen-containing gas components such as $H_2O$ and $CO_2$ other than NOx, in which the measurement is affected by oxygen existing in the measurement gas.

For example, the present invention is also applicable, for example, to gas sensors which are constructed to pump out $O_2$ produced by electrolysis of $CO_2$ or $H_2O$ by using the oxygen pump, and to gas sensors in which $H_2$ produced by electrolysis of $H_2O$ is pumping-processed by using a proton ion-conductive solid electrolyte.

It is a matter of course that the gas sensor according to the present invention is not limited to the embodiments described above, which may be embodied in other various forms without deviating from the gist or essential characteristics of the present invention.

What is claimed is:
1. A gas sensor comprising:
   a main pumping means for pumping-processing oxygen contained in a measurement gas introduced from an external space via a gas-introducing port into a processing space formed and comparted by solid electrolytes contacting with said external space so that a partial pressure of oxygen in said processing space is controlled to have a predetermined value at which a predetermined gas component as a measurement objective is not decomposable; and
   an electric signal-generating conversion means for making conversion into an electric signal corresponding to an amount of oxygen contained in said measurement gas after being pumping-processed by said main pumping means, wherein:
   a measurement gas component contained in said measurement gas is measured on the basis of said electric signal supplied from said electric signal-generating conversion means, said gas sensor further comprising:
      an electrode-free buffering space provided between said gas-introducing port and said processing space;
      a first diffusion rate-determining section, for giving a predetermined diffusion resistance to said measurement gas, provided upstream of said buffering space; and
      a second diffusion rate-determining section, for giving a predetermined diffusion resistance to said measurement gas, provided between said buffering space and said processing space.

2. The gas sensor according to claim 1, wherein:
   said electric signal-generating conversion means comprises a measuring pumping means for decomposing said measurement gas component contained in said measurement gas after being pumping-processed by said main pumping means, by means of catalytic action and/or electrolysis, and pumping-processing oxygen produced by said decomposition; and
   said measurement gas component contained in said measurement gas is measured on the basis of a pumping current flowing through said measuring pumping means in accordance with said pumping process effected by said measuring pumping means.

3. The gas sensor according to claim 1, wherein:
   said electric signal-generating conversion means comprises an oxygen partial pressure-detecting means for decomposing said measurement gas component contained in said measurement gas after being pumping-processed by said main pumping means, by means of catalytic action, and generating an electromotive force corresponding to a difference between an amount of oxygen contained in a reference gas and an amount of oxygen produced by said decomposition; and
   said measurement gas component contained in said measurement gas is measured on the basis of said electromotive force detected by said oxygen partial pressure-detecting means.

4. The gas sensor according to claim 1, wherein the volume of said buffering space is determined on the basis of at least each of said diffusion resistances of said first diffusion rate-determining section and said second diffusion rate-determining section.

5. The gas sensor according to claim 1, wherein:
   a front opening of said buffering space constitutes said gas-introducing port; and
   said first diffusion rate-determining section covers said gas-introducing port.

6. The gas sensor according to claim 1, wherein said first diffusion rate-determining section and said second diffusion rate-determining section are formed as narrow communication passages respectively.

7. The gas sensor according to claim 6, wherein a position of said communication passage for constructing said first diffusion rate-determining section is not coincident with a position of said communication passage for constructing said second diffusion rate-determining section, as viewed on projection planes opposed to a direction of introduction of said gas.

8. The gas sensor according to claim 1, wherein each of said first diffusion rate-determining section and said second diffusion rate-determining section is made of a porous member.

9. The gas sensor according to claim 1, wherein an area of a projection plane of said buffering space, which is opposed to a direction of introduction of said gas, is not less than an area of a projection plane of said processing space, which is opposed to said direction of introduction of said gas.

10. A gas sensor comprising:
   a main pumping means for pumping-processing oxygen contained in a measurement gas introduced from an external space via a gas-introducing port into a processing space formed and comparted by solid electrolytes contacting with said external space so that a partial pressure of oxygen in said processing space is controlled to have a predetermined value at which a predetermined gas component as a measurement objective is not decomposable; and
   a measuring pumping means for decomposing said measurement gas component contained in said measurement gas after being pumping-processed by said main pumping means, by means of catalytic action and/or electrolysis, and pumping-processing oxygen produced by said decomposition, wherein:
      said measurement gas component contained in said measurement gas is measured on the basis of a pumping current flowing through said measuring pumping means in accordance with said pumping process effected by said measuring pumping means, said gas sensor further comprising:
      a clogging-preventive section and a buffering space provided in series between said gas-introducing port and said processing space, wherein:
         said clogging-preventive section has its front opening which constitutes said gas-introducing port; and
         a diffusion rate-determining section for giving a predetermined diffusion resistance to said measurement gas is provided between said clogging-preventive section and said buffering space.

11. A gas sensor comprising:
   a main pumping means for pumping-processing oxygen contained in a measurement gas introduced from an external space via a gas-introducing port into a processing space formed and comparted by solid electrolytes contacting with said external space so that a partial pressure of oxygen in said processing space is controlled to have a predetermined value at which a predetermined gas component as a measurement objective is not decomposable; and
   an oxygen partial pressure-detecting means for decomposing said measurement gas component contained in said measurement gas after being pumping-processed by said main pumping means, by means of catalytic action, and generating an electromotive force corresponding to a difference between an amount of oxygen contained in a reference gas and an amount of oxygen produced by said decomposition, wherein:
      said measurement gas component contained in said measurement gas is measured on the basis of said electromotive force detected by said oxygen partial pressure-detecting means, said gas sensor further comprising:
      a clogging-preventive section and a buffering space provided in series between said gas-introducing port and a said processing space, wherein:
         said clogging-preventive section has its front opening which constitutes said gas-introducing port; and
         a diffusion rate-determining section for giving a predetermined diffusion resistance to said measurement gas is provided between said clogging-preventive section and said buffering space.

* * * * *